(12) United States Patent
Singh et al.

(10) Patent No.: US 12,008,977 B2
(45) Date of Patent: Jun. 11, 2024

(54) PERSONALIZED DISPLAY BRIGHTNESS BASED ON PUPIL SIZE

(71) Applicant: QUALCOMM Incorporated, San Diego, CA (US)

(72) Inventors: Shivendra Singh, Hyderabad (IN); Siva Ramesh Kumar Andey, Hyderabad (IN); Dinesh Singh Lourembam, Hyderabad (IN)

(73) Assignee: QUALCOMM Incorporated, San Diego, CA (US)

( * ) Notice: Subject to any disclaimer, the term of this patent is extended or adjusted under 35 U.S.C. 154(b) by 0 days.

(21) Appl. No.: 17/658,542

(22) Filed: Apr. 8, 2022

(65) Prior Publication Data

US 2023/0326427 A1 Oct. 12, 2023

(51) Int. Cl.
*G09G 5/10* (2006.01)
*A61B 3/11* (2006.01)

(52) U.S. Cl.
CPC ................ *G09G 5/10* (2013.01); *A61B 3/112* (2013.01); *G09G 2320/0626* (2013.01); *G09G 2354/00* (2013.01)

(58) Field of Classification Search
CPC ............ G09G 5/10; G09G 2320/0626; G09G 2354/00; G09G 2320/0693; A61B 3/112
See application file for complete search history.

(56) References Cited

U.S. PATENT DOCUMENTS

| | | | |
|---|---|---|---|
| 7,744,216 B1 * | 6/2010 | Uhlhorn | G06F 21/32 351/204 |
| 8,537,174 B2 * | 9/2013 | Capener | G09G 5/10 345/589 |
| 10,783,835 B2 | 9/2020 | Luna et al. | |
| 10,942,565 B2 * | 3/2021 | Ho | G06F 3/147 |
| 11,178,389 B2 | 11/2021 | Sinha et al. | |
| 11,798,460 B2 * | 10/2023 | Dai | G01J 1/32 |
| 2021/0134245 A1 | 5/2021 | Bonnier et al. | |
| 2021/0191512 A1 | 6/2021 | Ho et al. | |
| 2022/0051642 A1 | 2/2022 | Flach et al. | |
| 2022/0273171 A1 * | 9/2022 | Delaney | A61B 3/112 |

FOREIGN PATENT DOCUMENTS

WO  2020219063 A1  10/2020

OTHER PUBLICATIONS

International Search Report and Written Opinion—PCT/US2023/061329—ISA/EPO—dated Mar. 29, 2023.

\* cited by examiner

*Primary Examiner* — Antonio A Caschera
(74) *Attorney, Agent, or Firm* — QUALCOMM Incorporated

(57) ABSTRACT

In some aspects, a device may calibrate a brightness setting of the device for a user based on: displaying, by the device, first calibration content and modifying a luminance of a display while displaying the first calibration screen until a pupil size of the user satisfies a first target pupil size; and displaying, by the device, second calibration content and modifying the luminance of the display while displaying the second calibration screen until the pupil size of the user satisfies a second target pupil size. The device may calculate a metric value based upon pixel values of content to be displayed. The device may display, using a luminance that is adjusted based on the metric and in accordance with the brightness setting, the content. Numerous other aspects are described.

30 Claims, 11 Drawing Sheets

400

410 — Determine a first calibrated brightness value for a display screen based at least in part on: displaying first calibration content; adjusting a first brightness value of the display until a first measured pupil size of a user of the display matches a first target pupil size, wherein the first calibrated brightness value is based at least in part on the first brightness value of the display when the first measured pupil size of the user matches the first target pupil size 420 — Determine a second calibrated brightness value for the display based at least in part on: displaying second calibration content; adjusting a second brightness value of the display until a second measured pupil size of the user matches a second target pupil size, wherein the second calibrated brightness value is based at least in part on the second brightness value of the display when the second measured pupil size of the user matches the second target pupil size 430 — Display content 440 — Calculate a metric value for content to be displayed based upon pixel values of the content 450 — Adjust a brightness value of the display based at least in part on the first calibrated brightness value, the second calibrated brightness value, and the metric value

FIG. 4

PERSONALIZED DISPLAY BRIGHTNESS BASED ON PUPIL SIZE

FIELD OF THE DISCLOSURE

Aspects of the present disclosure generally relate to brightness control for a display of a device and, for example, to personalized display brightness that is based on a pupil size of a user.

BACKGROUND

Brightness is an attribute of visual perception in which a source appears to be radiating or reflecting light. In other words, brightness is the perception elicited by the luminance of a visual target. The perception is not linear to luminance and relies on the context of the viewing environment. An ambient light sensor is a component in smartphones, notebooks, other mobile devices, automotive displays and/or other displays. The ambient light sensor may be a photodetector that is used to sense the amount of ambient light present. A device may appropriately dim the device's display screen to match the amount of ambient light. This avoids having the screen be too bright in a dark environment, or too dim when the device is used outdoors in the daytime (e.g., in a bright environment). Dimming the screen of a device may also prolong a lifetime of a battery of the device.

SUMMARY

Some implementations described herein relate to a method. The method may include determining, by a device, a first calibrated brightness value for a display screen based at least in part on: displaying, by the device, first calibration content; and adjusting, by the device, a first brightness value of the display until a first measured pupil size of a user of the display matches a first target pupil size, where the first calibrated brightness value is based at least in part on the first brightness value of the display when the first measured pupil size of the user matches the first target pupil size. The method may include determining, by the device, a second calibrated brightness value for the display based at least in part on: displaying, by the device, second calibration content; and adjusting, by the device, a second brightness value of the display until a second measured pupil size of the user matches a second target pupil size, where the second calibrated brightness value is based at least in part on the second brightness value of the display when the second measured pupil size of the user matches the second target pupil size. The method may include calculating, by the device, a metric value for content to be displayed based upon pixel values of the content. The method may include adjusting, by the device, a brightness value of the display based at least in part on the first calibrated brightness value, the second calibrated brightness value, and the metric value.

Some implementations described herein relate to a device. The device may include one or more memories and one or more processors coupled to the one or more memories. The one or more processors may be configured to obtain a brightness setting of a display screen associated with the device for a user based at least in part on: displaying first calibration content and modifying a luminance of the display screen of the device while displaying the first calibration content until a pupil size of the user satisfies a first target pupil size; and displaying second calibration content and modifying the luminance of the display screen while displaying the second calibration content until the pupil size of the user satisfies a second target pupil size. The one or more processors may be configured to calculate a metric value based at least in part on pixel values of content to be displayed. The one or more processors may be configured to adjust the luminance for the display screen based at least in part on the metric value and in accordance with the brightness setting. The one or more processors may be configured to display, via the display screen and using the adjusted luminance of the display, the content.

Some implementations described herein relate to a non-transitory computer-readable medium that stores a set of instructions for a device. The set of instructions, when executed by one or more processors of the device, may cause the device to calibrate a brightness setting of the device for a user based at least in part on: displaying first calibration content using a first brightness value of a display screen of the device that achieves a first target pupil size of the user; displaying second calibration content using a second brightness value of the display screen of the device that achieves a second target pupil size of the user; and displaying a user input option to adjust at least one of the first brightness value or the second brightness value. The set of instructions, when executed by one or more processors of the device, may cause the device to calculate a metric value based at least in part on pixel values of content to be displayed. The set of instructions, when executed by one or more processors of the device, may cause the device to display, via the display screen and using an adjusted brightness value, the content, wherein the adjusted brightness value is based at least in part on the metric value and is adjusted in accordance with the brightness setting.

Some implementations described herein relate to an apparatus. The apparatus may include means for calibrating a brightness setting of the apparatus for a user based at least in part on: displaying first calibration content and modifying a luminance of a display screen of the apparatus while displaying the first calibration content until a pupil size of the user satisfies a first target pupil size; and displaying second calibration content and modifying the luminance of the display screen while displaying the second calibration content until the pupil size of the user reaches a second target pupil size. The apparatus may include means for calculating a metric value based at least in part on pixel values of content to be displayed by the apparatus. The apparatus may include means for adjusting the luminance for the display screen based at least in part on the metric value and in accordance with the brightness setting.

Aspects generally include a method, apparatus, system, computer program product, non-transitory computer-readable medium, user device, user equipment, wireless communication device, and/or processing system as substantially described with reference to and as illustrated by the drawings and specification.

The foregoing has outlined rather broadly the features and technical advantages of examples according to the disclosure in order that the detailed description that follows may be better understood. Additional features and advantages will be described hereinafter. The conception and specific examples disclosed may be readily utilized as a basis for modifying or designing other structures for carrying out the same purposes of the present disclosure. Such equivalent constructions do not depart from the scope of the appended claims. Characteristics of the concepts disclosed herein, both their organization and method of operation, together with associated advantages will be better understood from the following description when considered in connection with the accompanying figures. Each of the figures is provided for the purposes of illustration and description, and not as a definition of the limits of the claims.

BRIEF DESCRIPTION OF THE DRAWINGS

So that the above-recited features of the present disclosure can be understood in detail, a more particular description, briefly summarized above, may be had by reference to aspects, some of which are illustrated in the appended drawings. It is to be noted, however, that the appended drawings illustrate only certain typical aspects of this disclosure and are therefore not to be considered limiting of its scope, for the description may admit to other equally effective aspects. The same reference numbers in different drawings may identify the same or similar elements.

FIGS. 4-6 are flowcharts of example processes associated with personalized display brightness based on pupil size.

DETAILED DESCRIPTION

Figure 1:
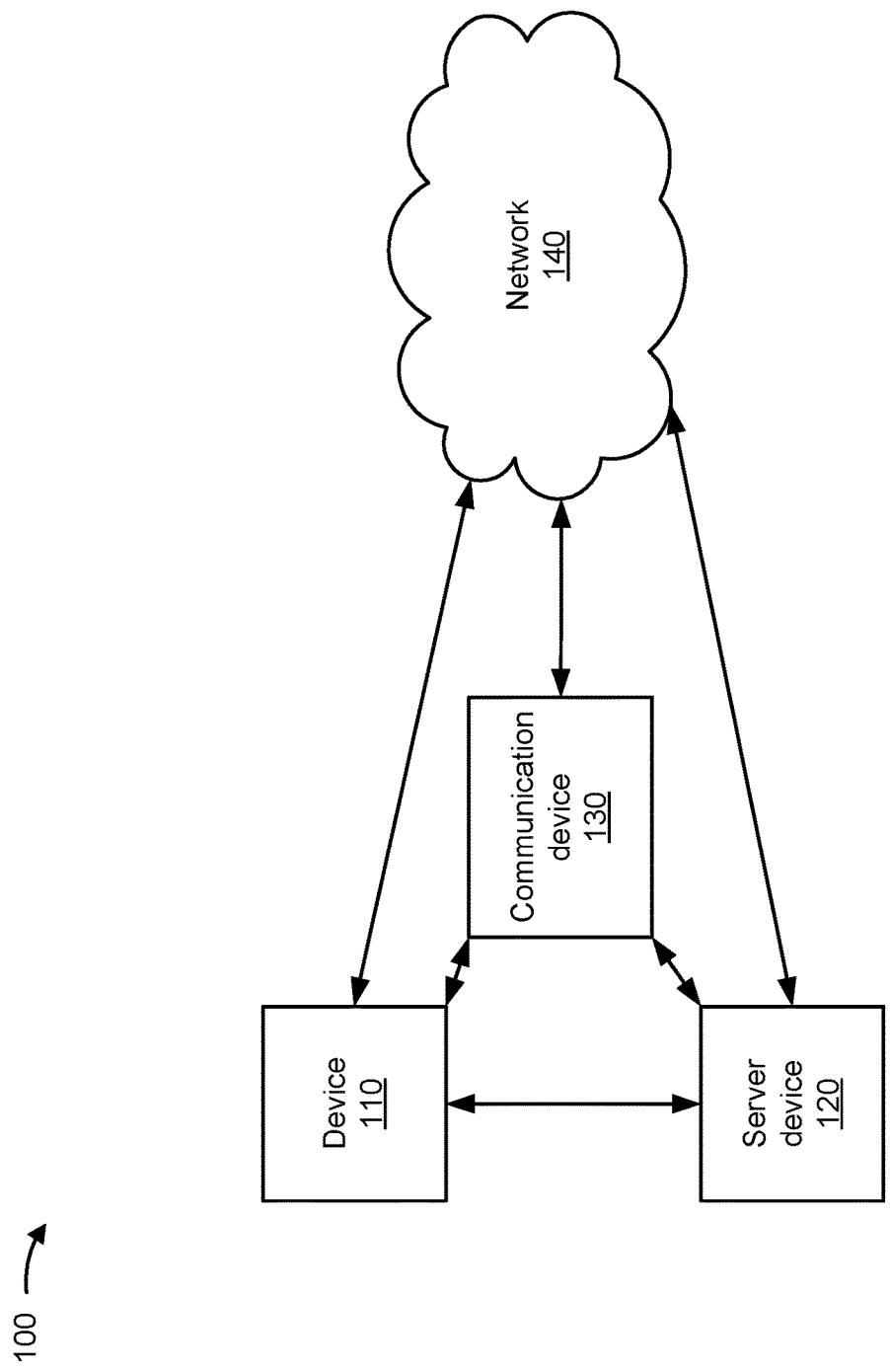
FIG. 1 is a diagram illustrating an example environment in which personalized display brightness that is based on a pupil size of a user described herein may be implemented, in accordance with the present disclosure.

Various aspects of the disclosure are described more fully hereinafter with reference to the accompanying drawings. This disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. One skilled in the art should appreciate that the scope of the disclosure is intended to cover any aspect of the disclosure disclosed herein, whether implemented independently of or combined with any other aspect of the disclosure. For example, an apparatus may be implemented or a method may be practiced using any number of the aspects set forth herein. In addition, the scope of the disclosure is intended to cover such an apparatus or method which is practiced using other structure, functionality, or structure and functionality in addition to or other than the various aspects of the disclosure set forth herein. It should be understood that any aspect of the disclosure disclosed herein may be embodied by one or more elements of a claim.

In some cases, a device may automatically adjust a brightness (e.g., a luminous intensity) of a display screen. For example, the device may measure an amount of ambient light. The device may adjust the brightness of the display screen based on the amount of ambient light (e.g., to increase the brightness of the display screen in environments with more ambient light and to decrease the brightness of the display screen in environments with less ambient light). However, in some cases, ambient light may not be relevant for brightness determinations by the device. For example, the device may be a wearable device, such as a head mounted display or a headset, that blocks ambient light from reaching the display screen of the device. As a result, the device may be unable to automatically adjust the brightness of the display using an amount of ambient light. In such examples, a user may have to manually adjust the brightness of the display screen for different content or different applications. For example, the user may have to manually increase the brightness of the display screen when the content or application being displayed shows a dim or dark environment. Conversely, the user may have to manually decrease the brightness of the display screen when the content or application being displayed shows a bright (e.g., a white or approximately white) environment. This may consume processing recourses and/or memory resources of the device and/or may result in a poor user experience associated with multiple manual adjustments of the brightness value of the display screen.

Additionally, different users may be associated with different sensitivities to light. For example, for a given brightness value (e.g., a luminous intensity) of a display screen, a first user may be comfortable viewing the display screen, but a second user may be unconformable viewing the display screen (e.g., the second user may have to strain their eyes to view the display screen at the given brightness value). In other words, automatic brightness determinations by a device may not be personalized to a given user. As a result, the determined brightness setting may cause strain to a user's eyes, resulting in a poor user experience and/or in the user having to manually adjust the brightness setting of the device.

Some implementations described herein enable personalized display brightness that is based on a pupil size of a user. For example, a device (e.g., a wearable device) may calibrate a brightness setting for a user based at least in part on a measured pupil size of the user in various scenarios. For example, the device may display first calibration content (e.g., having a background that has a pixel value (e.g., a red, green, blue (RGB) value) that corresponds to a bright color (e.g., white), such as (255, 255, 255) in an RGB color code scheme). The device may periodically or repeatedly (e.g., every 10 seconds, 12 seconds, 8 seconds, 4, seconds, or another amount of time) modify a brightness value used to display the first calibration screen and measure a pupil size of the user after each modification of the brightness value. The device may continue to modify the brightness value until the pupil size of the user matches (or is within a threshold amount of) a target pupil size for bright (e.g., white) screens. The target pupil size may be a typical or expected pupil size in bright light, such as between 2 millimeters and 4 millimeters. The device may store the brightness value of the first calibration content that caused the pupil size of the user to match, or be close to, the target pupil size for bright screens. In some aspects, the device may receive a user input adjusting the brightness value after performing the above operations. The device may repeat these operations using second calibration content (e.g., having a background that has a pixel value that corresponds to a dark color (e.g., black), such as (0, 0, 0)). As a result, the device may obtain a brightness setting that includes an optimized brightness value and pupil size for the user for bright content (e.g., based on displaying the first calibration content) and an optimized brightness value and pupil size for the user for dark content (e.g., based on displaying the second calibration content).

The calibrated brightness setting may be used to adjust the brightness value for the display screen based on the content being displayed or to be displayed. For example, the device may calculate a metric value based on pixel values of the content being displayed or to be displayed. The device may determine a relationship between the metric value of the content to be displayed and corresponding metric values of the first calibration content (e.g., approximately 255 using the RGB color code scheme) and the second calibration content (e.g., approximately 0 using the RGB color code scheme). The device may determine the brightness value to be used to display the content based at least in part on the relationship, a calibrated brightness value for bright content, and a calibrated brightness value for dark content. The device may display the content using the determined brightness value.

As a result, a brightness value used by the device may be personalized to the user. For example, calibrating the brightness setting of the device based at least in part on pupil measurements of the user may enable the device to personalize brightness determinations made by the device to a particular user. Additionally, the device may automatically adjust a brightness value used to display content without requiring an ambient light measurement. Further, the device may automatically adjust a brightness value used by the device without requiring a measurement of a pupil size of the user while the user is viewing the content (e.g., based on calibrating the brightness setting using pupil measurements of the user). Therefore, the techniques and operations described herein may conserve processing and/or memory resources that would have otherwise been used by a user manually adjusting the brightness of the display screen of the device. Additionally, the techniques and operations described herein may improve a user experience by personalizing the automatic brightness determinations made by the device to a given user.

FIG. 1 is a diagram illustrating an example environment 100 in which personalized display brightness that is based on a pupil size of a user described herein may be implemented, in accordance with the present disclosure. As shown in FIG. 1, environment 100 may include a device 110, a server device 120, a communication device 130, and a network 140. Devices of environment 100 may interconnect via wired connections, wireless connections, or a combination of wired and wireless connections.

The device 110 includes one or more devices capable of receiving, generating, storing, processing, and/or providing information associated with personalized display brightness that is based on a pupil size of a user, as described elsewhere herein. The device 110 may be an electronic device including, or associated with, a display with an adjustable brightness. In some aspects, the device 110 may be connected to the display via a wired or wireless connection. The device 110 may include a communication device and/or a computing device. For example, the device 110 may be, or may include, a virtual reality (VR) headset, a wireless communication device, a mobile phone, a user equipment, a laptop computer, a tablet computer, a wearable communication device (e.g., a smart wristwatch, a pair of smart eyeglasses, a smart wristband, smart jewelry, and/or a head mounted display), and/or a similar type of device. While the device 110 may be described herein as being "wearable," the techniques and operations described herein may be applied by any device that includes a display with an adjustable brightness (e.g., the device 110 does not need to be worn to perform the techniques and operations described herein). In some aspects, the device 110 may be controlled by, or configured by, the communication device 130. For example, in some cases, the communication device 130 may perform one or more operations described herein, such as controlling or determining a calibration of a brightness setting for the device 110, and may provide information to the device 110 to enable the device 110 to operate in accordance with the calibrated brightness setting.

The server device 120 includes one or more devices capable of receiving, generating, storing, processing, providing, and/or routing information associated with personalized display brightness that is based on the pupil size of the user, as described elsewhere herein. The server device 120 may include a communication device and/or a computing device. For example, the server device 120 may include a server, such as an application server, a client server, a web server, a database server, a host server, a proxy server, a virtual server (e.g., executing on computing hardware), or a server in a cloud computing system. In some implementations, the server device 120 includes computing hardware used in a cloud computing environment.

The communication device 130 includes one or more devices capable of receiving, generating, storing, processing, and/or providing information associated with personalized display brightness that is based on a pupil size of a user, as described elsewhere herein. In some aspects, the communication device 130 may be connected to the display via a wired or wireless connection. The communication device 130 may include a communication device and/or a computing device. For example, the communication device 130 may be, or may include, a wireless communication device, a mobile phone, a user equipment, a laptop computer, a tablet computer, a wearable communication device (e.g., a smart wristwatch, a pair of smart eyeglasses, a smart wristband, smart jewelry, and/or a head mounted display), and/or a similar type of device. In some aspects, the device 110 may be control, or configure, the device 110. For example, in some cases, the communication device 130 may perform one or more operations described herein, such as controlling or determining a calibration of a brightness setting for the device 110, and may provide information to the device 110 to enable the device 110 to operate in accordance with the calibrated brightness setting.

The network 140 includes one or more wired and/or wireless networks. For example, the network 140 may include a wireless wide area network (e.g., a cellular network or a public land mobile network), a local area network (e.g., a wired local area network or a wireless local area network (WLAN), such as a Wi-Fi network), a personal area network (e.g., a Bluetooth network), a near-field communication network, a telephone network, a private network, the Internet, and/or a combination of these or other types of networks. The network 140 enables communication among the devices of environment 100.

The number and arrangement of devices and networks shown in FIG. 1 are provided as an example. In practice, there may be additional devices and/or networks, fewer devices and/or networks, different devices and/or networks, or differently arranged devices and/or networks than those shown in FIG. 1. Furthermore, two or more devices shown in FIG. 1 may be implemented within a single device, or a single device shown in FIG. 1 may be implemented as multiple, distributed devices. Additionally, or alternatively, a set of devices (e.g., one or more devices) of environment 100 may perform one or more functions described as being performed by another set of devices of environment 100.

Figure 2:
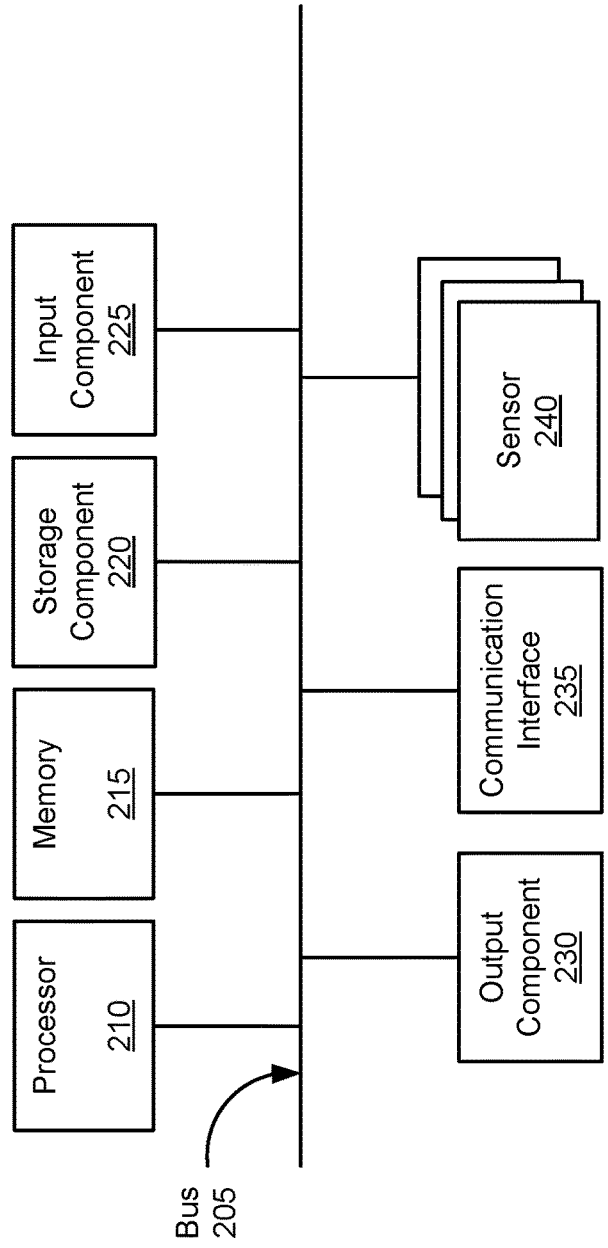
FIG. 2 is a diagram illustrating example components of one or more devices shown in FIG. 1, such as a device or a server device, in accordance with the present disclosure.

FIG. 2 is a diagram illustrating example components of a device 200, in accordance with the present disclosure. Device 200 may correspond to the device 110, the server device 120, and/or the communication device 130. In some aspects, the device 110, the server device 120, and/or the communication device 130 may include one or more devices 200 and/or one or more components of device 200. As shown in FIG. 2, device 200 may include a bus 205, a processor 210, a memory 215, a storage component 220, an input component 225, an output component 230, a communication interface 235, and/or a sensor 240.

Bus 205 includes a component that permits communication among the components of device 200. Processor 210 is implemented in hardware, firmware, or a combination of hardware and software. Processor 210 is a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), or another type of processing component. In some aspects, processor 210 includes one or more processors capable of being programmed to perform a function. Memory 215 includes a random access memory (RAM), a read only memory (ROM), and/or another type of dynamic or static storage device (e.g., a flash memory, a magnetic memory, and/or an optical memory) that stores information and/or instructions for use by processor 210.

Storage component 220 stores information and/or software related to the operation and use of device 200. For example, storage component 220 may include a hard disk (e.g., a magnetic disk, an optical disk, a magneto-optic disk, and/or a solid state disk), a compact disc (CD), a digital versatile disc (DVD), a floppy disk, a cartridge, a magnetic tape, and/or another type of non-transitory computer-readable medium, along with a corresponding drive.

Input component 225 includes a component that permits device 200 to receive information, such as via user input (e.g., a touch screen display, a keyboard, a keypad, a mouse, a button, a switch, and/or a microphone). Additionally, or alternatively, input component 225 may include a component for determining a position or a location of device 200 (e.g., a global positioning system (GPS) component or a global navigation satellite system (GNSS) component) and/or a sensor for sensing information (e.g., an accelerometer, a gyroscope, an actuator, or another type of position or environment sensor). Output component 230 includes a component that provides output information from device 200 (e.g., a display, a speaker, a haptic feedback component, and/or an audio or visual indicator).

Communication interface 235 includes a transceiver-like component (e.g., a transceiver and/or a separate receiver and transmitter) that enables device 200 to communicate with other devices, such as via a wired connection, a wireless connection, or a combination of wired and wireless connections. Communication interface 235 may permit device 200 to receive information from another device and/or provide information to another device. For example, communication interface 235 may include an Ethernet interface, an optical interface, a coaxial interface, an infrared interface, a radio frequency interface, a universal serial bus (USB) interface, a wireless local area interface (e.g., a Wi-Fi interface), and/or a cellular network interface.

Sensor 240 includes one or more wired or wireless devices capable of detecting and/or measuring a pupil size of the user. For example, sensor 240 may include a camera, a near-infrared (NIR) camera, an optical sensor, an eye tracking sensor, a pupilometer, or a similar type of device. As another example, sensor 240 includes one or more wired or wireless devices capable of measuring a brightness value of a display screen.

Device 200 may perform one or more processes described herein. Device 200 may perform these processes based on processor 210 executing software instructions stored by a non-transitory computer-readable medium, such as memory 215 and/or storage component 220. A computer-readable medium is defined herein as a non-transitory memory device. A memory device includes memory space within a single physical storage device or memory space spread across multiple physical storage devices.

Software instructions may be read into memory 215 and/or storage component 220 from another computer-readable medium or from another device via communication interface 235. When executed, software instructions stored in memory 215 and/or storage component 220 may cause processor 210 to perform one or more processes described herein. Additionally, or alternatively, hardwired circuitry may be used in place of or in combination with software instructions to perform one or more processes described herein. Thus, aspects described herein are not limited to any specific combination of hardware circuitry and software.

In some aspects, device 200 includes means for performing one or more processes described herein and/or means for performing one or more operations of the processes described herein. For example, device 200 may include means for determining a first calibrated brightness value for a display screen based at least in part on: displaying first calibration content; and adjusting a first brightness value of the display until a first measured pupil size of a user of the display matches a first target pupil size, wherein the first calibrated brightness value is based at least in part on the first brightness value of the display when the first measured pupil size of the user matches the first target pupil size; means for determining a second calibrated brightness value for the display based at least in part on: displaying second calibration content; and a second brightness value of the display until a second measured pupil size of the user matches a second target pupil size, wherein the second calibrated brightness value is based at least in part on the second brightness value of the display when the second measured pupil size of the user matches the second target pupil size; means for calculating a metric value for content to be displayed based upon pixel values of the content; and/or means for adjusting a brightness value of the display based at least in part on the first calibrated brightness value, the second calibrated brightness value, and the metric value; among other examples. Additionally, or alternatively, device 200 may include means for obtaining a brightness setting of a display screen associated with the device for a user based at least in part on: displaying first calibration content and modifying a luminance of the display screen of the device while displaying the first calibration content until a pupil size of the user satisfies a first target pupil size; and displaying second calibration content and modifying the luminance of the display screen while displaying the second calibration content until the pupil size of the user satisfies a second target pupil size; means for calculating a metric value based at least in part on pixel values of content to be displayed; means for adjusting the luminance for the display screen based at least in part on the metric value and in accordance with the brightness setting; and/or means for displaying, using the adjusted luminance, the content; among other examples. Additionally, or alternatively, device 200 may include means for calibrating a brightness setting of the device for a user based at least in part on: displaying first calibration content using a first brightness value of a display screen of the device that achieves a first target pupil size of the user; displaying second calibration content using a second brightness value of the display screen of the device that achieves a second target pupil size of the user; and displaying a user input option to adjust at least one of the first brightness value or the second brightness value; means for calculating a metric value based at least in part on pixel values of content to be displayed; and/or means for displaying, using an adjusted brightness value, the content, wherein the adjusted brightness value is based at least in part on the metric value and is adjusted in accordance with the brightness setting; among other examples. In some aspects, such means may include one or more components of device 200 described in connection with FIG. 2, such as bus 205, processor 210, memory 215, storage component 220, input component 225, output component 230, communication interface 235, and/or sensor 240.

The number and arrangement of components shown in FIG. 2 are provided as an example. In practice, device 200 may include additional components, fewer components, different components, or differently arranged components than those shown in FIG. 2. Additionally, or alternatively, a set of components (e.g., one or more components) of device 200 may perform one or more functions described as being performed by another set of components of device 200.

Figure 3A:
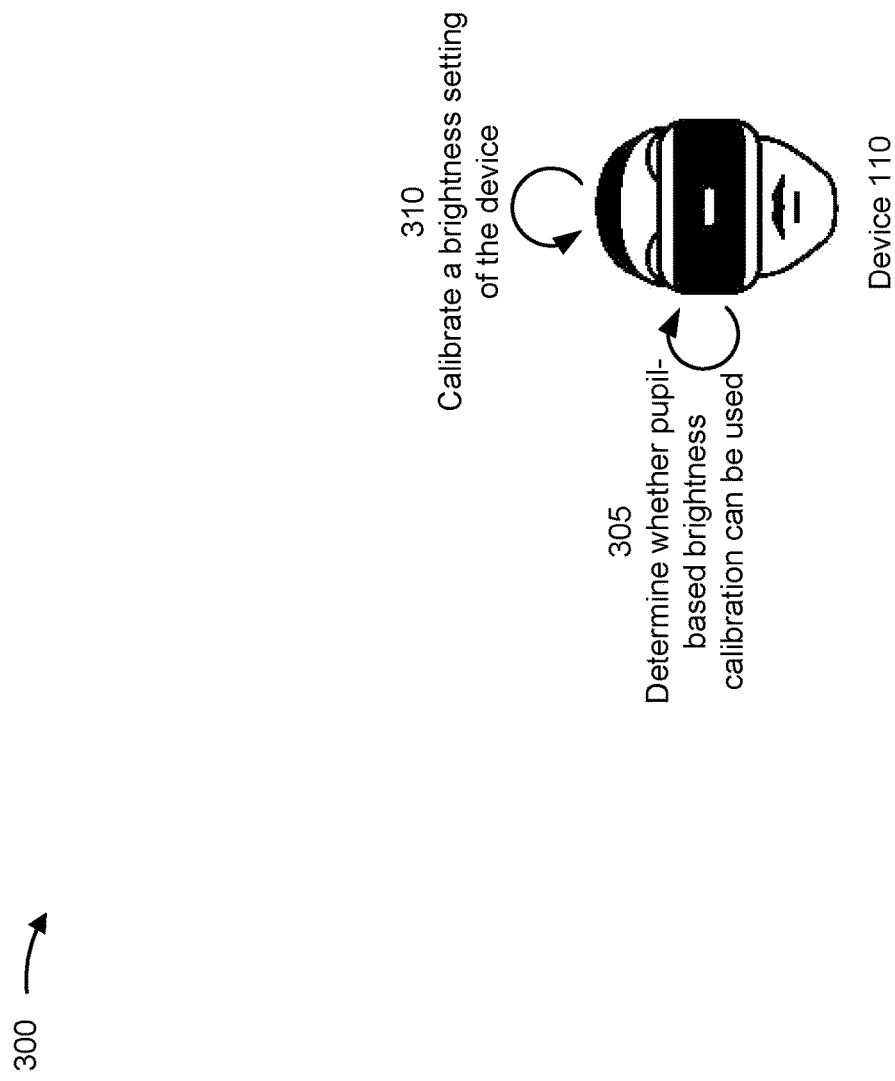
FIGS. 3A-3D are diagrams illustrating an example associated with personalized display brightness that is based on a pupil size of a user, in accordance with the present disclosure.
Figure 3B:
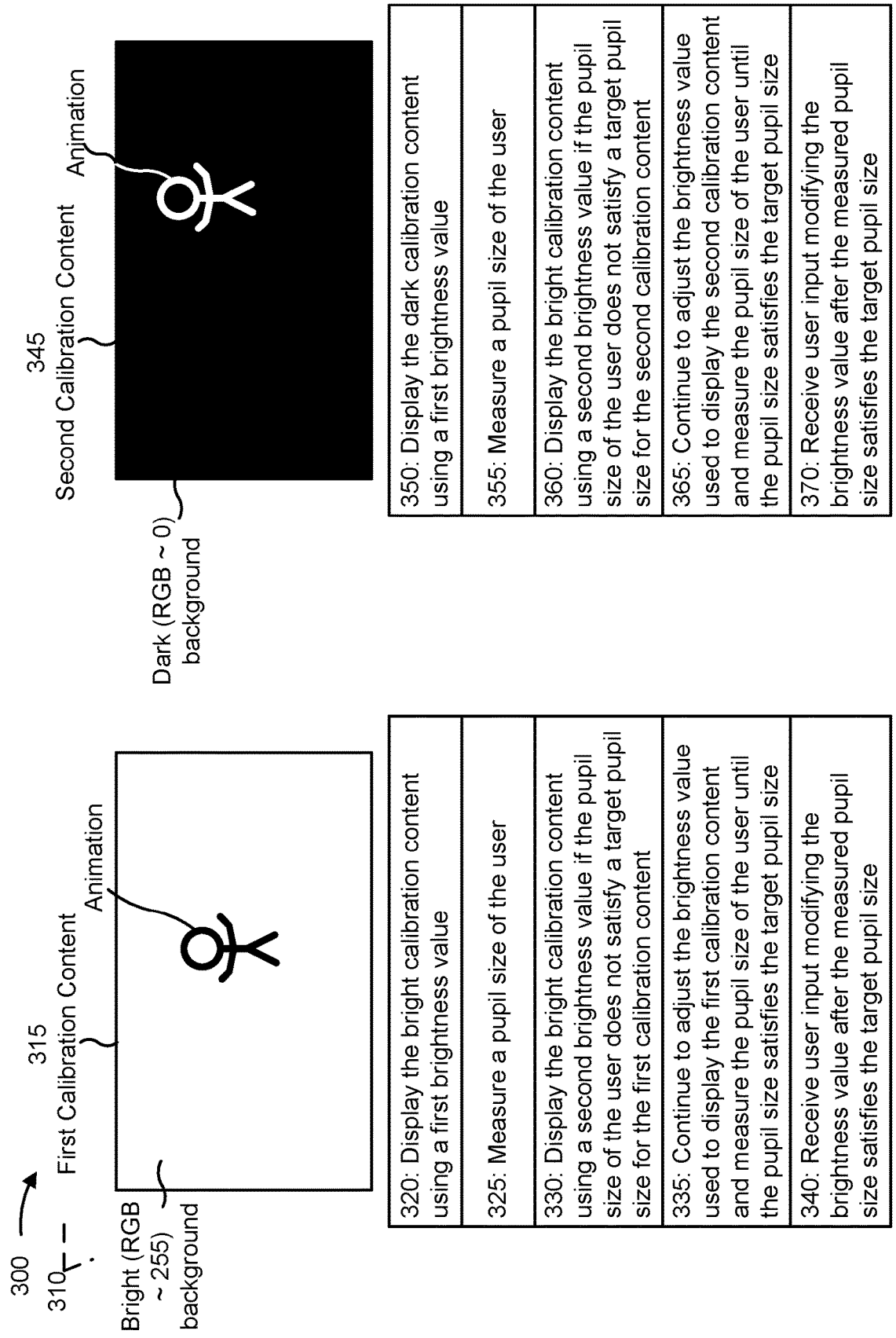
Figure 3C:
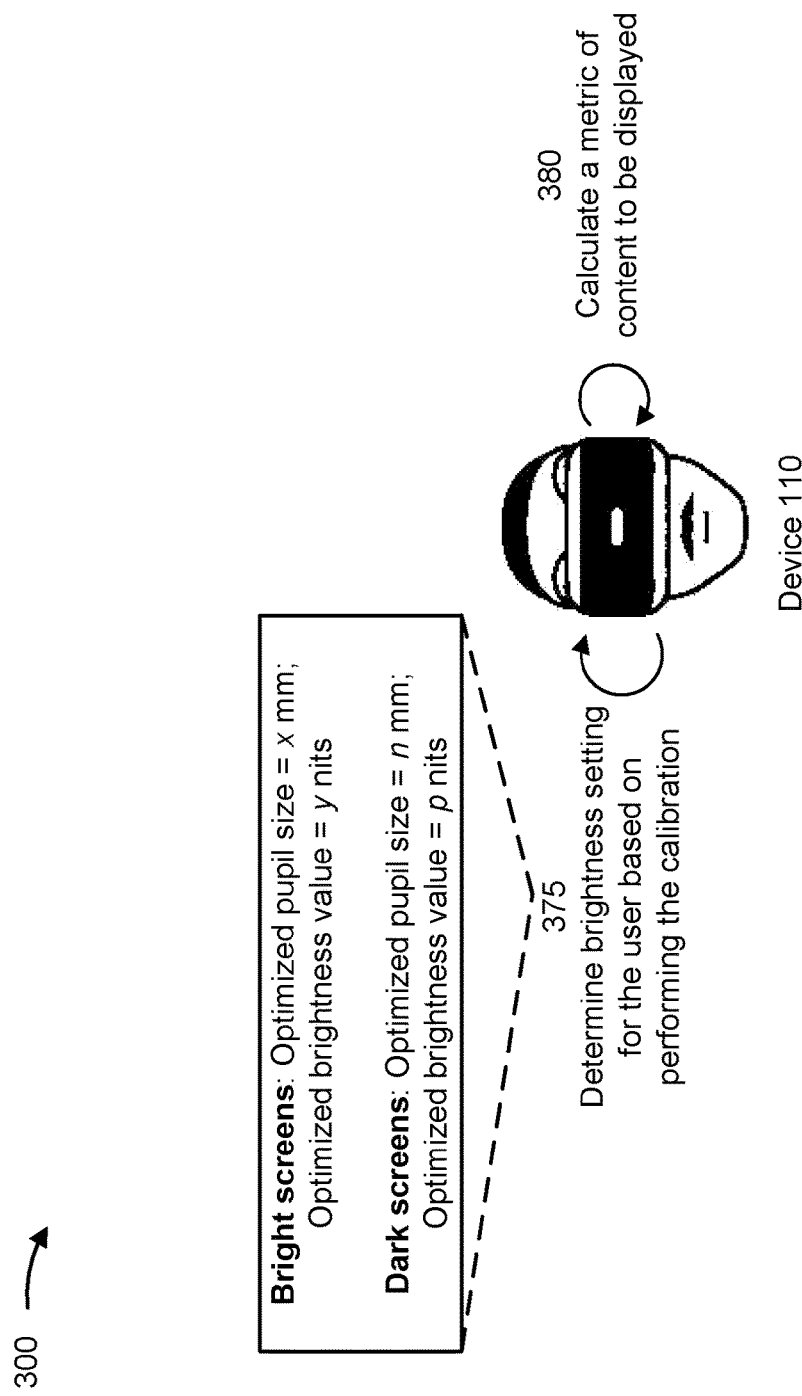

FIGS. 3A-3D are diagrams illustrating an example 300 associated with personalized display brightness that is based on a pupil size of a user, in accordance with the present disclosure. As shown in FIGS. 3A-3C, example 300 includes the device 110 performing one or more operations associated with adjusting a brightness of a display of the device based at least in part on a calibrated brightness setting (e.g., that is calibrated based at least in part on a pupil size of the user). In some aspects, the device 110 and the server device 120 (not shown in FIGS. 3A-3D) may communicate via a wireless (e.g., cellular) connection of the device 110 to communicate information associated with providing a personalized display brightness that is based on a pupil size of a user.

The device 110 may include a display (e.g., a single display screen or multiple display screens, such as two display screens). The display may be associated with an adjustable brightness value (e.g., the device 110 may be enabled to adjust a brightness of the display). The brightness value may also be referred to herein as a brightness level or a luminance (or luminous intensity) of a display screen. As used herein, "brightness" of the display may be associated with a luminance of the display (e.g., brightness may be the perception elicited by the luminance of the display). For example, the luminance (or luminous intensity or brightness value) of the display may be measured in candela per square meter, which may also be referred to as a nit. The brightness value may refer to a value of a brightness setting of a display wherein for instance, larger brightness values indicate a larger luminance of the display. In other words, the brightness value may be indicative of a brightness setting from a range of brightness settings at which the display may be operated or driven. A corresponding range of brightness values may be defined to reflect the range of brightness settings at which the display is operable. The range of brightness values may correspond to actual display luminance via a strictly increasing functional dependence such as a linear dependence, but not limited thereto. The brightness values may be defined as a set of discrete brightness values, such as integer brightness values covering the range of luminance at which the display may operate.

Brightness may differ from a color or pixel value associated with the display. The pixel value may indicate a color of a given pixel. For example, for greyscale images, pixel values may range between 0 (e.g., corresponding to the color black) and 255 (e.g., corresponding to the color white). For color images, an RGB triplet may be used to indicate values for (red, green, and blue) respectively. For example, for color images, the color white may be represented by a pixel value of (255, 255, 255) and the color black may be represented by a pixel value of (0, 0, 0). For example, a pixel value may include one or more numbers in the range of 0 to 255, where the number represents an intensity of each of the color components with 0 being the lowest intensity and 255 being highest intensity. For example, a RGB triplet of (A, B, C) may represent a color where red has an intensity of A, green has an intensity of B, and blue has an intensity of C. The RGB color triplet may be a 24-bit color code where 8 bits are assigned to each color of red, blue, and green (e.g., hence the scale of 0 to 255 because 8 bits are capable of indicating unsigned integer values from 0 to 255). In greyscale, the pixel value may be an 8-bit value (e.g., may be a single value from 0 to 255). While some examples are described herein in connection with the RGB color space, other color spaces may be used in a similar manner as described herein, such as a YCbCr color space (e.g., where Y is a luma component, Cb is a blue-difference chroma component, and Cr is a red-difference chroma component). In the present disclosure, pixel values refer to content, e.g., one or more (color) component values in a color space such as RGB or YCbCr, to be displayed by a (hardware) pixel of the display while the brightness value or brightness setting refers to an (overall) luminance of the display, i.e. an (electrical) operating parameter of the display. In some examples, the brightness value or brightness setting may indicate a (maximum) driving current or voltage for (hardware) pixels of the display as described below. In other words, a brightness value or brightness setting in the present disclosure is independent of the content to be displayed.

The device 110 may be configured to adjust the brightness value (e.g., in nits) of the display screen and the pixel value for each pixel of the display screen. In some aspects, the device 110 may be enabled to adjust the brightness value of the display screen via a backlight of the display, such as for liquid crystal display (LCD) screens, among other examples. In some other aspects, the device 110 may not include a backlight, and the device 110 may be enabled to adjust the brightness value of the display screen via an amount of electric current provided to an element of the display, such as for light-emitting diode (LED) screens, organic LED (OLED) screens, or retinal projection displays, among other examples.

As compared to a brightness value or brightness setting, a brightness as used in the present disclosure refers to the perception elicited by the luminance of the display. Different from the brightness value or brightness setting, the (perceived) brightness depends on the content being displayed. By way of example, a light grey pixel is perceived as being brighter than a dark grey pixel when the display is operated at the same brightness value/setting (e.g., brightness setting and brightness value may be used interchangeably herein). In contrast, a dark grey pixel may be perceived brighter than a light grey pixel if the display is operated at a (significantly) higher brightness value/setting for the dark grey pixel than for the light grey pixel. Consequently, the brightness (e.g., the perceived brightness) of a (e.g., hardware) pixel depends on both, the content being displayed and the brightness value/setting of the display.

Moreover, a brightness (e.g., a perceived brightness) of a region or an entire display screen is considered in the present disclosure in terms of a cumulative brightness of the involved pixels of the display screen. Thus, the brightness of a (region of a) display screen depends on the displayed (region of a) content frame, screen, or video sequence as well as the brightness value/setting of the display.

A metric (e.g., a statistical average of pixel values, such as an average of pixel values, a mean value, and/or a median value, as explained in more detail elsewhere herein) may be defined to determine the cumulative brightness of a (region of a) display screen displaying content. The metric may be applied to a particular region such as a region of interest of a frame, an entire frame or even multiple frames of a video sequence. The metric may be applied to all pixels or samples of the region or frame or only a subset (e.g., subsampled set), of the pixels or samples of the region or frame. The metric may further include time averaging over multiple frames.

In sum, a metric may be defined such that a value of the metric determined for (e.g., a region of) content displayed on (e.g., a corresponding region of) the display screen is indicative of the brightness (e.g., the perceived brightness) of the displayed content if displayed at a fixed brightness value/setting of the display. In other words, the metric may be defined to decouple the brightness (e.g., the perceived brightness) of displayed content from the brightness value/setting of the display by defining the metric to be calculated based on pixel values of the content without regard to the brightness value/setting of the display. As a consequence, the brightness (e.g., the perceived brightness) may be determined as a (separable) function of a content-dependent value of the metric and a content-independent brightness value/setting of the display.

In turn, the techniques disclosed herein permit a content-dependent adjustment of a brightness value/setting of a display to be more agreeable to an individual user. The disclosed techniques determine one or more content-dependent calibrated brightness values for one or more display screens, such as a single screen or dual screens of a VR device, as reference values for content-dependent display adjustments. In some examples, content (or calibration) frames are used for the calibration which have largely disparate metric values to calibrate the display screen in terms of (mostly) dark as well as (mostly) light content being displayed. Calibration frames may be selected or determined from content frames. For example, a user may be watching a video or playing a game which contains frames suitable for use as calibration frames; these frames are determined by their content and are assigned as calibration frames. The device 110 may opportunistically calibrate based upon determining that a content frame is suitable for use as a calibration frame. For example, the device 110 may determine that a content frame is suitable to serve as calibration content. The characteristic of the content frame(s) may be based at least in part on pixel values of the content frame(s). For example, the device 110 may determine that pixel values (e.g., an average pixel value) of content frame(s) satisfies (e.g., is greater than or equal to) a bright light threshold. Therefore, the device 110 may determine that the content can be used as a first calibration content described in more detail elsewhere herein. In this way, the device 110 may identify content frame(s) that can be displayed to achieve similar pupillary characteristics in users as the first calibration content and/or the second calibration content described in more detail below. This may improve a user experience by enabling the user to view content frame(s) during calibration, rather than viewing the same calibration screen each time the device 110 performs the calibration.

Between the two extreme cases, an all-black and an all-white frame, calibration frames may be selected to represent opposite ends of the range of possible metric values. In other words, calibration frames may be selected whose respective metric values lie within a specific margin, such as less than half (e.g., 25, 10, or 5 percent) of the range of possible metric values, from the respective minimum or maximum metric value. Additionally, a minimum distance from the respective minimum or maximum metric value, such as 0.1, 1, or 2 percent of the range, may be observed for the selected calibration frames to avoid an all-black or all-white calibration frame. Corresponding criteria may be applied for calibration content including multiple frames, such as video sequences or animated content, by applying a corresponding metric to the multiple frames.

As shown in FIG. 3A, and by reference number 305, the device 110 may determine whether pupil-based brightness calibration can be used by the device 110. The following description discloses techniques for application to a single display screen viewed with one or both eyes of the user. In some aspects, the device 110 may separately calibrate and adjust individual display screens for the left eye and the right eye of a user. By separately calibrating and adjusting display screens for the left and right eyes of a user, different brightness perceptions by the left and right eyes can be accounted for and an overall viewing experience may be improved.

For example, the device 110 may determine that the brightness value can be calibrated and adjusted using a pupil size of the user based at least in part on a dilation time associated with a dilation of a pupil of the user. For example, the device 110 may measure and/or track a pupil size of the user to determine an amount of time (e.g., the dilation time) that the user's pupil takes to dilate. The dilation time may refer to the amount of time that the user's pupil takes to adjust a size of the pupil after a change in brightness or color of the display screen.

The device 110 may compare the dilation time associated with the user to a threshold. The threshold may be a dilation time that is used for all users. In some aspects, the threshold may be specific to the user (e.g., the device 110 may determine an average dilation time of the user based on past use of the device and may determine the threshold based at least in part on the average dilation time of the user). In some aspects, the device 110 may receive an indication of a value of the threshold from the server device 120. In some other aspects, a value of the threshold may be configured (e.g., pre-configured prior to a first use of the device 110) in a memory or storage of the device 110.

If the dilation time associated with the user satisfies (e.g., is less than or equal to) the threshold, then the device 110 may determine that the brightness value can be calibrated and adjusted using a pupil size of the user. If the dilation time associated with the user does not satisfy the threshold, then the device 110 may determine that the brightness value cannot be calibrated and adjusted using the pupil size of the user. For example, if the dilation time associated with the user is high, then it may take an extended amount of time for the user's pupils to dilate or adjust to different brightness levels. Therefore, the device 110 may be unable to calibrate a brightness value/setting correctly or accurately for the user (e.g., as explained elsewhere herein in more detail) when the dilation time associated with the user is high.

For example, in some cases, such as when the user is intoxicated, the user may be associated with a delayed pupillary response to changes in brightness perceived by the user. In such examples, the device 110 may be unable to calibrate a brightness setting correctly or accurately for the user because of the delayed pupillary response. Therefore, by determining whether pupil-based brightness calibration can be used by the device 110, the device 110 may conserve processing resources and/or memory resources that would have otherwise been used attempting to calibrate the brightness setting when the dilation time associated with the user does not satisfy the threshold. If the device 110 determines that the brightness value cannot be calibrated and adjusted using the pupil size of the user, then the device 110 may cause a notification to be displayed that indicates that an automatic brightness adjustment feature (e.g., that is based at least in part on a pupil size of the user, as described elsewhere herein) of the device 110 is deactivated. In such examples, the device 110 may refrain from calibrating and/or adjusting the brightness of the display as described herein. If the device 110 determines that the dilation time associated with the user satisfies the threshold, then the device 110 may proceed with calibrating and adjusting the brightness of the display as described herein.

The device 110 may determine whether pupil-based brightness calibration can be used by the device 110, as described above, at a startup time of the device 110 (e.g., when a user powers on the device 110). As another example, the device 110 may determine whether pupil-based brightness calibration can be used by the device 110, as described above, at the start of a calibration phase for the pupil-based brightness calibration (e.g., prior to performing the calibration as described in more detail below).

As shown by reference number 310, the device 110 may calibrate a brightness value/setting of the device 110 for the user (e.g., for a specific user). The calibration results may be stored on the device or remotely, such as on the server device 120. The calibration results may be associated with the specific user via a unique user identification. Such a user identification may be based on user credentials such as login and password information input by the user to the device during calibration, on voice recognition, and/or retina or iris scan/detection of one or more eyes of the user. The user identification may be used at a later time by the device 110 to identify the current user of the display and/or device and automatically adjust a brightness value/setting of the device according to the calibration results of the identified user. In this context, retina or iris scan/detection using optical and/or infrared sensors may improve a user experience by enabling the device 110 to identify the user without the user inputting information, such as a login, password, or other identifying information.

The brightness value/setting may be calibrated based at least in part on measurements of a pupil size of the user. As depicted and described in more detail in connection with FIG. 3B, the brightness value/setting may include a first luminance of the display optimized for the user for first calibration content 315 including one or more first calibration frames and a second luminance of the display optimized for the user for second calibration content 345 including one or more second calibration frames. In one example, the first calibration content 315 may include a bright calibration frame (e.g., "bright" referring to the pixel values of the calibration frame, or more specifically, to a metric value for the calibration frame indicating a bright screen, such as within a margin from the metric value for an all-white frame as described above), and the second calibration content 345 may include a dark calibration frame (e.g., "dark" referring to the pixel values of the calibration frame, or more specifically, to a metric value for the calibration frame indicating a dark screen, such as within a margin from the metric value for an all-black frame as described above), as depicted and described in more detail in connection with FIG. 3B. Performing calibration and adjustment based on bright and dark calibration frames as described in more detail herein allows automatically adjusting the brightness value/setting of a display to the sensitivity range of an individual user with regard to the perceived brightness. In some other examples, the first calibration content may be associated with a first color (e.g., green), and the second calibration content may be associated with a second color (e.g., red). Performing calibration and adjustment based on different colors of the calibration frames allows automatically adjusting the brightness value/setting of a display to different color sensitivities of the user. The two calibration and adjustment techniques may be combined by using additional calibration frames and defining a (further) metric that is indicative of the color dependence of the perceived brightness. By way of example, a two-dimensional metric with a first component being indicative of a luminance (Y in the YCrCb color space) based brightness as described herein and a second component being indicative of a chrominance (Cr, Cb in the YCrCb color space) based brightness may be defined.

In another example, the first calibration content may include a first calibration frame for a first display screen of the display, e.g., a left-eye display, and the second calibration content may include a second calibration frame for a second display screen, e.g., a right-eye display. The first and second calibration frames may be identical such that a relative brightness calibration/adjustment of the first and second display screens can be achieved. In one particular example, separate calibrations (and adjustments) may be performed for the first and second display screens, each including a calibration with respect to a bright calibration frame and a calibration with respect to a dark calibration frame. The respective bright and dark calibration frames may be identical or different for the left and right eyes. In other words, the calibration and adjustment described herein in greater detail can be independently applied to each eye of the user.

For example, the device 110 may identify a first target pupil size (or first target range of pupil sizes) associated with bright or light colored frames and a second target pupil size (or second target range of pupil sizes) associated with dim or dark colored frames. For example, the pupil of a user may adjust itself based on an amount of light received by the pupil (e.g., the pupil may automatically expand in dark environments to allow more light to enter the user's eye and may automatically contract in bright environments to allow less light to enter the user's eye). For example, the pupil size of a user may typically be within a given range in bright light (e.g., 2 millimeters to 4 millimeters). Similarly, for a given user, the pupil size may be within a given range in the dark (e.g., 4 millimeters to 8 millimeters). The first target pupil size (or first target range of pupil sizes) and the second target pupil size (or second target range of pupil sizes) may be based at least in part on the typical pupil size of humans in bright and dark environments, respectively. In some aspects, the first target pupil size (or first target range of pupil sizes) and the second target pupil size (or second target range of pupil sizes) may be based at least in part on demographics of the user, such as age, sex, race, ethnicity, and/or other demographic information. In some aspects, the device 110 may receive an indication of the first target pupil size (or first target range of pupil sizes) and the second target pupil size (or second target range of pupil sizes) from the server device 120.

In some aspects, another device, such as the server device 120 or the communication device 130, may control or otherwise direct the calibration, as described herein. In such examples, the device 110 may receive, from the other device, results of the calibration, such as a brightness setting, as described in more detail elsewhere herein. As used herein, the device 110 "obtaining" the brightness setting or calibration results may refer to the device 110 performing the calibration, as described in more detail elsewhere herein, or receiving the brightness setting or calibration results from another device, such as the server device 120 or the communication device 130, among other examples.

The device 110 may perform the calibration, as described in more detail elsewhere herein, based at least in part on detecting one or more calibration events. A calibration event may include detecting that the device 110 has been powered on (e.g., the device 110 may calibrate the brightness setting each time the device 110 is powered on). As another example, a calibration event may include detecting an expiration of a timer. For example, the device 110 may periodically calibrate the brightness setting (e.g., once per day, once per week, or once every 3 weeks, among other examples). As another example, a calibration event may include detecting that a new application or game is executing on the device 110 (e.g., a new application or game is being displayed by the device 110). For example, the device 110 may calibrate the brightness setting when switching between applications or games executing on the device 110. As another example, a calibration event may include detecting a don and/or doff event (e.g., detecting that a user has put on and/or removed the device 110). For example, the device 110 may calibrate the brightness setting after each time the device 110 (or a component associated with the device 110, such as a headset or component including the display screen) is removed and/or put on by a user. As another example, a calibration event may include detecting a new user of the device, i.e. a user for whom no results of a previous calibration are available to the device. Detection of a new user may be based on user credentials, voice detection/recognition, and/or retina or iris scan/detection as described above.

As shown in FIG. 3B, the calibration of the brightness setting for the user may include displaying first calibration content 315. As shown in FIG. 3B, in some examples, the first calibration content 315 may include one or more calibration frames with a background having a first pixel value that approximately corresponds to white (e.g., is within a margin, such as 5, 10, or 25 percent of the complete range of pixel values, from the pixel value for white). For multi-component pixel values such as RGB or YCrCb pixel values, a distance norm, average difference, or the like may be calculated to determine that the first pixel value approximately (e.g., within a distance margin) corresponds to white. For example, the pixel value of the background of the first calibration content 315 may be approximately 255 or (255, 255, 255) (e.g., using an RGB triplet code) or may have an average pixel value that satisfies a bright light threshold (e.g., the bright light threshold for individual or all color components may be 220, 230, 245, 250, or similar values). In other words, the background of the first calibration content 315 may be the color white or similar colors to cause light or bright colors to be displayed to the user. The first calibration content 315 may include an animation having a pixel value that corresponds to a color other than white. For example, the animation may have a pixel value that approximately (e.g., within a margin for the distance norm, average difference, or the like) corresponds to black (e.g., 0 or (0, 0, 0)). For example, the animation may have a color that contrasts with the approximately white background. In this example, the first calibration content 315 may include a plurality of calibration frames. In some aspects, the same metric defined for adjusting the brightness value/setting of the display screen as explained in more detail elsewhere may be applied to determine whether the first calibration content/frame(s) correspond(s) to a bright calibration frame as described above.

In some aspects, the animation may be a dynamic animation that moves on the display screen of the device 110 while the first calibration content 315 is displayed. In some other aspects, the animation may be static animation (e.g., that does not move on the display screen of the device 110 while the first calibration content 315 is displayed). The animation may provide an object for the user to focus on while the first calibration content 315 is displayed. Providing an object to focus on may improve the ability of the user to adjust to the brightness and/or color of the first calibration content 315 (e.g., enabling the user to focus on the animation may reduce an amount of time required for the user's pupils to adjust to the brightness and/or color of the first calibration content 315). This may improve the calibration of the brightness setting by ensuring that the pupil size of the user is fully adjusted when measurements are taken by the device 110, as explained in more detail elsewhere herein.

As shown by reference number 320, the device 110 may display the first calibration content 315 using a first brightness value/setting (e.g., in nits) of the respective display screen. The device 110 may display the first calibration content 315 using the first brightness value/setting for a first interval or period of time (e.g., 10 seconds, 12 seconds, 8 seconds, 4, seconds, 2 seconds, or another amount of time). As shown by reference number 325, the device 110 may measure a pupil size of the user after displaying the first calibration content 315 using the first brightness value/setting (e.g., after the first interval or period of time). For example, the first interval or period of time may provide time for the user's pupils to adjust to the color of the first calibration content 315 and/or to the first brightness value/setting used to display the first calibration content 315. The device 110 may measure the pupil size of the user using the sensor 240, such as an NIR camera, an optical camera, or another device.

The device 110 may compare the measurement of the pupil size of the user to the first target pupil size (or the first target range of pupil sizes). For example, the device 110 may determine whether the measurement of the pupil size matches, or is within a threshold amount of, the first target pupil size (or is within the first target range of pupil sizes). If the device 110 determines that the measurement of the pupil size matches, or is within the threshold amount of, the first target pupil size (or is within the first target range of pupil sizes), then the device 110 may determine that the (personal) brightness setting of the user for the first calibration content (e.g., bright screens or a particular color) is calibrated.

As shown by reference number 330, if the device 110 determines that the measurement of the pupil size does not match, or is not within the threshold amount of, the first target pupil size (or is not within the first target range of pupil sizes), then the device 110 may display the first calibration content 315 using a second brightness value/setting (e.g., in nits). The device 110 may display the first calibration content 315 using the second brightness value/setting for a second interval or period of time (e.g., 10 seconds or another amount of time) which may have the same length as the first interval or period of time. The device 110 may measure the pupil size of the user after displaying the first calibration content 315 using the second brightness value/setting (e.g., after the second interval or period of time) to determine if the pupil size of the user matches, or is within the threshold amount of, the first target pupil size.

In some aspects, the second brightness value may be greater than the first brightness value (e.g., if the measured pupil size of the user is greater than the first target pupil size). In some other aspects, the second brightness value may be less than the first brightness value (e.g., if the measured pupil size of the user is less than the first target pupil size). For example, the device 110 may determine whether to increase or decrease the brightness value used to display the first calibration content 315 based at least in part on whether the pupil size of the user needs to increase or decrease to reach the first target pupil size.

As shown by reference number 335, the device 110 may continue to adjust the brightness value used to display the first calibration content 315 and measure the pupil size of the user until the pupil size of the user satisfies the first target pupil size (e.g., until the pupil size of the user matches or is within the threshold amount of the first target pupil size). In other words, the device 110 may repeatedly or periodically (e.g., every 10 seconds) adjust the brightness value of the device 110 while the first calibration content 315 is displayed. The device 110 may measure the pupil size of the user after each adjustment of the brightness value until the pupil size of the user is approximately (e.g., is within the threshold amount of) the first target pupil size.

The device 110 may determine that a measured pupil size of the user matches, or is within the threshold amount of, the first target pupil size (or is within the first target range of pupil sizes). As a result, the device 110 may determine that the brightness setting of the user for the first calibration content 315 (e.g., bright screens or a particular color) is calibrated. The device 110 may identify the brightness value that was used to display the first calibration content 315 when the measured pupil size of the user satisfied the first target pupil size. The brightness value may be a first calibrated brightness value associated with the brightness setting for the user. For example, the first calibrated brightness value may be a brightness value at which the eye(s) of the user is (are) estimated to be comfortable when viewing bright or light (e.g., white) content (e.g., content frame(s) having a pixel value that is close to, or approximately, 255 or (255, 255, 255)) or content of a particular color, as determined by the device 110 by measuring the pupil size of the user, as described above.

In some aspects, as shown by reference number 340, the device 110 may receive a user input modifying the brightness value/setting (e.g., the first calibrated brightness value/setting) after the measured pupil size of the user satisfies the first target pupil size. For example, after calibrating the brightness setting for bright or light (e.g., white) content as described in connection with reference numbers 320 through 335, the device 110 may display the first calibration content 315 using the first calibrated brightness value. The device 110 may display a request for the user to modify the brightness value/setting used by the device 110. For example, the request may be "calibration complete for bright content, please adjust the brightness if needed to finalize the calibration." If the device 110 receives a user input indicating an adjustment to the brightness value/setting (e.g., the first calibrated brightness value), then the device 110 may modify the first calibrated brightness value/setting in accordance with the user input. In this way, the calibration performed by the device 110 may consider user input, thereby improving a likelihood that the first calibrated brightness value results in a comfortable brightness for the user when bright or light (e.g., white) content frames are displayed by the device 110.

In addition to identifying the first calibrated brightness value, the device 110 may identify the pupil size of the user when the first calibrated brightness value is used to display the first calibration content 315. For example, if a user input indicates an adjustment to the first calibrated brightness value, then the device 110 may measure a pupil size of the user (e.g., after displaying the first calibration content 315 using the adjusted first calibrated brightness value) to identify or update the first target pupil size of the user for bright or light (e.g., white) content or a particular color. In this way, the first target pupil size of the user and the first calibrated brightness value may be specific to the user and may indicate a pupil size and/or brightness value at which the user is comfortable when bright or light (e.g., white) content frames are displayed by the device 110.

As shown in FIG. 3B, the calibration of the brightness setting for the user may include displaying second calibration content 345. As shown in FIG. 3B, the second calibration content 345 may include one or more calibration frames with a background having a second pixel value that approximately corresponds to black (e.g., is within a margin, such as 5, 10, or 25 percent of the complete range of pixel values, from the pixel value for black). For multi-component pixel values such as RGB or YCrCb pixel values, a distance norm, average difference, or the like may be calculated to determine that the second pixel value approximately (e.g., within a distance margin) corresponds to black. For example, the pixel value of the background of the second calibration content 345 may be approximately 0 or (0, 0, 0) (e.g., using an RGB triplet code) or may less than or equal to a dark light threshold (e.g., the dark light threshold for individual or all color components may be 50, 40, 25, 10, 5, or similar values). In other words, the background of the second calibration content 345 may be the color black or similar colors to cause dark or dim colors to be displayed to the user. The second calibration content 345 may include an animation having a pixel value that corresponds to a color other than black. For example, the animation may have a pixel value that approximately (e.g., within a margin for the distance norm, average difference, or the like) corresponds to white (e.g., 255 or (255, 255, 255)). For example, the animation may have a color that contrasts with the approximately black background. In this example, the second calibration content 345 may include a plurality of calibration frames. In some aspects, the same metric defined for adjusting the brightness value/setting of the display screen as explained in more detail elsewhere may be applied to determine whether the second calibration content/frame(s) correspond(s) to a dark calibration frame as described above.

As shown in FIG. 3B, the device 110 may calibrate a second calibrated brightness value/setting and identify or update a second target pupil size for the user for dark content in a similar (or the same) manner as described above in connection with the first calibration content 315. For example, as shown by reference number 350, the device 110 may display the second calibration content 345 using a second brightness value/setting (e.g., in nits). The second brightness value/setting may be equal to the first brightness value/setting initially used as the starting brightness value/setting for the first calibration content. Alternatively, the second brightness value/setting may initially be set to the first calibrated brightness value to accelerate the calibration. The device 110 may display the second calibration content 345 using the second brightness value/setting for a first interval or period of time (e.g., 10 seconds or another amount of time). As shown by reference number 355, the device 110 may measure a pupil size of the user after displaying the second calibration content 345 using the first brightness value/setting (e.g., after the first interval or period of time).

The device 110 may compare the measurement of the pupil size of the user to a second target pupil size (or a second target range of pupil sizes) that is associated with dark content. If the device 110 determines that the measurement of the pupil size matches, or is within the threshold amount of, the second target pupil size (or is within the second target range of pupil sizes), then the device 110 may determine that the brightness setting of the user for the second calibration content 345 (e.g., dark screens or another particular color) is calibrated.

As shown by reference number 360, if the device 110 determines that the measurement of the pupil size does not match, or is not within the threshold amount of, the second target pupil size (or is not within the second target range of pupil sizes), then the device 110 may display the second calibration content 345 using a second brightness value/setting (e.g., in nits). As shown by reference number 365, the device 110 may continue to adjust the brightness value used to display the second calibration content 345 and measure the pupil size of the user until the pupil size of the user satisfies the second target pupil size (e.g., until the pupil size of the user matches, or is within the threshold amount of, the second target pupil size). In other words, the device 110 may repeatedly or periodically (e.g., every 10 seconds) adjust the brightness value of the device 110 while the second calibration content 345 is displayed. The device 110 may measure the pupil size of the user after each adjustment of the brightness value until the pupil size of the user is approximately (e.g., is within the threshold amount of) the second target pupil size.

The device 110 may determine that a measured pupil size of the user matches, or is within the threshold amount of, the second target pupil size (or is within the second target range of pupil sizes). As a result, the device 110 may determine that the brightness setting of the user for the second calibration content (e.g., dark screens or another particular color) is calibrated. The device 110 may identify the brightness value that was used to display the second calibration content 345 when the measured pupil size of the user satisfied the second target pupil size. The brightness value may be a second calibrated brightness value associated with the brightness setting for the user. For example, the second calibrated brightness value may be a brightness value at which the eye(s) of the user is (are) comfortable when viewing dark or dim (e.g., dark) content (e.g., content frame(s) having a pixel value that is close to, or approximately, 0 or (0, 0, 0)) or content of another particular color, as determined by the device 110 by measuring the pupil size of the user, as described above.

In some aspects, as shown by reference number 370, the device 110 may receive a user input modifying the brightness value/setting (e.g., the second calibrated brightness value/setting) after the measured pupil size of the user satisfies the second target pupil size. The device 110 may display a request for the user to modify the brightness value/setting used by the device 110. If the device 110 receives a user input indicating an adjustment to the brightness value/setting (e.g., the second calibrated brightness value), then the device 110 may modify the second calibrated brightness value/setting in accordance with the user input.

In addition to identifying the second calibrated brightness value, the device 110 may identify the pupil size of the user when the second calibrated brightness value is used to display the second calibration content 345. For example, if a user input indicates an adjustment to the second calibrated brightness value, then the device 110 may measure a pupil size of the user (e.g., after displaying the second calibration content 345 using the adjusted second calibrated brightness value) to identify or update the second target pupil size of the user for dark or dim (e.g., black) content or another particular color. In this way, the second target pupil size of the user and the second calibrated brightness value may be specific to the user and may indicate a pupil size and/or brightness value at which the user is comfortable when dark or dim (e.g., black) content frames are displayed by the device 110.

As a result, after calibrating the brightness setting for the user, the device 110 may identify a first calibrated brightness value and optionally a first (updated) target pupil size for the user (e.g., for bright content) and a second calibrated brightness value and optionally a second (updated) target pupil size for the user (e.g., for dark content). This may provide the device 110 with bounds for the brightness values used by the device 110. For example, because the first calibration content 315 is mostly white, the first calibration content 315 may approximate the brightest or lightest content that may be displayed by the device 110. Similarly, because the second calibration content 345 is mostly black, the second calibration content 345 may approximate the darked or dimmest content that may be displayed by the device 110. As a result, the device 110 may use the first calibrated brightness value and the second calibrated brightness value as reference points for adjusting the brightness value/setting used by the device 110 to display various content (e.g., that has pixel values somewhere between the pixel values of the first calibration content 315 (e.g., 255) and the second calibration content 345 (e.g., 0)), as described in more detail elsewhere herein. In some aspects, default brightness value can be used as the reference point for the darked or dimmest content, in which case the operations regarding the second calibration content 345 may be omitted.

In some aspects, the first calibration content 315 and/or the second calibration content 345 may be images or videos that are determined to have one or more characteristics that make the content suitable to be used as calibration content. For example, the device 110 may determine that content is suitable to serve as calibration content (e.g., the first calibration content 315 and/or the second calibration content 345). The characteristic of the content may be based at least in part on pixel values of the content. For example, the characteristic may be an average pixel value of the content. For example, the device 110 may determine that pixel values (e.g., an average pixel value) of content satisfies (e.g., is greater than or equal to) the bright light threshold. Therefore, the device 110 may determine that the content can be used as the first calibration content 315 (e.g., in a similar manner as described above). As another example, the device 110 may determine that pixel values (e.g., an average pixel value) of content is less than or equal to the dark light threshold. Therefore, the device 110 may determine that the content can be used as the second calibration content 345 (e.g., in a similar manner as described above). In this way, the device 110 may identify content that can be displayed to achieve similar pupillary characteristics in users as the first calibration content 315 and/or the second calibration content 345. This may improve a user experience by enabling the user to view content during calibration, rather than viewing the same calibration screen each time the device 110 performs the calibration. Other metrics than an average pixel value may be used. The same metric may be used for determining that content can be used as calibration content as is used for later adjustment of the brightness value/setting for displaying content on the calibrated display.

As shown in FIG. 3C, and by reference number 375, the device 110 may determine the calibrated brightness setting for the user based at least in part on performing the calibration, as described above. For example, the calibrated brightness setting may indicate two values: a first calibrated brightness value (e.g., n nits) and a second calibrated brightness value (e.g., p nits). Additionally, the calibrated brightness setting may indicate a first (updated) target pupil size (e.g., x millimeters) and a second (updated) target pupil size (e.g., y millimeters). As described in more detail above, the first (updated) target pupil size and the first calibrated brightness value may be identified based at least in part on performing the calibration using the first calibration content 315 (e.g., the first calibrated brightness value may be the first calibrated brightness value described above). In other words, the first (updated) target pupil size and the first calibrated brightness value may be calibrated to be a comfortable pupil size and brightness value for the user when viewing bright content (e.g., content frame(s) having an average pixel value or color code of approximately 255 or (255, 255, 255)). Similarly, the second (updated) target pupil size and the second calibrated brightness value may be identified based at least in part on performing the calibration using the second calibration content 345 (e.g., the second calibrated brightness value may be the second calibrated brightness value described above). In other words, the second (updated) target pupil size and the second calibrated brightness value may be calibrated to be a comfortable pupil size and brightness value for the user when viewing dark content (e.g., content frame(s) having an average pixel value or color code of approximately 0 or (0, 0, 0)). In some examples, default values can be used as the second optimized pupil size and the second optimized brightness value.

The device 110 may store the brightness setting as being associated with a user profile of the user. For example, after determining the brightness setting for a given user, the device 110 may store the brightness setting in a user profile for the user. In this way, the device 110 may load the brightness setting for the given user at a future time without having to perform an additional calibration to determine the brightness setting (e.g., thereby conserving processing resources associated with the device 110). For example, the device 110 may detect that the user profile has been loaded or signed into. For example, the user profile may be associated with a credential. The credential may be a username and/or password, a unique identifier, a personal identification number (PIN), and/or a biometric identifier (e.g., a fingerprint scan, a retina or iris scan, a facial scan, a voice-based identifier (e.g., a voice print), or another biometric identifier), among other examples. The device 110 may detect a credential. For example, a user input may indicate the credential and/or the device 110 may perform an action to obtain the credential, such as performing biometric scan. The device 110 may determine whether the credential is authenticated for the identified user profile. For example, the device 110 may compare the credential provided by the user to a credential stored by the device 110. If the credentials match (or are similar), then the device 110 may determine that the credential provided by the user is authenticated. The device 110 may load the user profile (e.g., including the brightness setting) based on authenticating the credential.

As shown by reference number 380, the device 110 may calculate a metric of content to be displayed. In some aspects, the device 110 may calculate a metric of content to be displayed prior to displaying the content. Alternatively, the device 110 may calculate a metric of content after (e.g., shortly after) displaying the content. The metric may be based at least in part on pixel values of one or more content frames (e.g., of the content being displayed or to be displayed by the device 110). The content frame(s) may be associated with content of a display screen of the device 110. For example, the content may be associated with an application executing on the device 110, a game, a video, a page, an image, and/or other content being displayed by the device 110. For example, the device 110 may display the content via the display of the device 110. The device 110 may calculate the metric of the content to identify a theme or context of the color (e.g., on a color scale from 0 to 255, as described above) of the content being displayed.

In some aspects, the metric may be an average pixel value. For example, "average pixel value" may refer to an average pixel value for all pixels of the display screen over one or more frames of the content being displayed (or to be displayed) by the device 110. In some examples, the average pixel value may be determined based on a portion of the pixels (e.g. representative pixels) of the display screen. "Frame" may refer to a still image of the content at a given time (e.g., similar to a frame of a moving picture or video).

For example, the device 110 may calculate the average pixel value of content over a sample window (e.g., the sample window may include one or more content frames). To calculate the average pixel value for the content being displayed or to be displayed by the device 110, the device 110 may calculate, for a given content frame, a frame pixel value. "Frame pixel value" may refer to an average pixel value of all, or a portion of, of the pixels of the given frame. The device 110 may calculate the average pixel value of the content based at least in part on an average of the frame pixel values of the one or more frames (e.g., the one or more frames included in the sample window) across color components of the pixel values. For example, for a pixel, the device 110 may calculate a greyscale pixel value for the pixel using an RGB color code value (e.g., an RGB triplet) associated with the pixel. The greyscale pixel value may be a single value on a scale of 0 to 255, as described above, and may provide an indication as to whether the color of the pixel is closer to the color white (e.g., a pixel value of 255) or black (e.g., a pixel value of 0). For example, for the pixel associated with an RGB triplet of ($R_1$, $G_1$, $B_1$), the device 110 may calculate the greyscale pixel value as the average $$\frac{R_1 + G_1 + B_1}{3}.$$

The device 110 may calculate greyscale pixel values for all, or a portion of, pixels of a frame in a similar manner. Although the above example is described as using an average value of the R, G, and B values of the RGB triplet to calculate a greyscale pixel value, a weighted average may also be used by the device 110. For example, rather than averaging the RGB triplet values $$\left(\text{e.g., as } \frac{R_1 + G_1 + B_1}{3}\right)$$

to calculate the greyscale pixel value, the device 110 may apply one or more weights when calculating the greyscale pixel value. For example, the device 110 may apply one or more coefficients to the R, G, and B values (for example, a coefficient of 0.2126, 0.299, or another value to the R value, a coefficient of 0.7152, 0.0587, or another value to the G value, and a coefficient of 0.0722, 0.114, or another value to the B value) (e.g., to account for different color sensitivity of the human eye). Additionally, or alternatively, the device 110 may raise one or more of the R, G, or B values to a power. For example, to calculate a greyscale pixel value for a given RGB triplet, the device 110 may use a weighted average according to the formula: $(0.2126 \times R_1^{2.2} + 0.7152 \times G_1^{2.2} + 0.0722 \times B_1^{2.2})^{1/2.2}$. The weighted average formula provided above is an example and other weighted average formulas may be used by the device 110 in a similar manner. Therefore, as used herein, calculating an average pixel value, an average frame value, or a greyscale pixel value may refer to calculating an actual average or a weighted average, as described herein. Alternatively, a luminance component (e.g., Y in the YCrCb color space) may be used as a greyscale pixel value on input to a corresponding metric or averaging function for determining the average pixel value of content over a sample window.

The device 110 may calculate a greyscale pixel value (e.g., the frame pixel value) for the frame by averaging the greyscale pixel values for all, or a portion of, pixels of the frame. For example, for a frame including n pixels, the device 110 may calculate the frame pixel value using the equation:

$$\frac{\left(\frac{R_1+G_1+B_1}{3}\right)+\left(\frac{R_2+G_2+B_2}{3}\right)+\left(\frac{R_3+G_3+B_3}{3}\right)+\ldots+\left(\frac{R_n+G_n+B_n}{3}\right)}{n}$$

While the above formula uses an average value of the R, G, and B values for each pixel, a weighted average may also be used (e.g., in a similar manner as described above). The device 110 may calculate the average pixel value for the content based at least in part on averaging the frame pixel values of the one or more frames included in the sample window for the content. Therefore, the average pixel value for the content may indicate a greyscale pixel value (e.g., on the scale of 0 to 255) for the content. In some other aspects, rather than using greyscale pixel values (e.g., single values on the scale of 0 to 255), the device 110 may calculate the average pixel value for the content using RGB triplet values. For example, for a frame, the device 110 may average the red values for all pixels of the frame to obtain an average red value, average the green values for all pixels of the frame to obtain an average green value, and average the blue values for all pixels of the frame to obtain an average blue value. This may provide an average RGB triplet value for the frame (e.g., the frame pixel value). In such examples, the device 110 may calculate the average pixel value for the content based at least in part on averaging the RGB triplet values (e.g., the frame pixel values) of the one or more frames included in the sample window for the content.

The average pixel value for the content may provide an indication of the color or theme of the content being displayed by the device 110. For example, if the average pixel value for the content is closer to 0, this may provide an indication that the content is darker or dimmer (e.g., closer to the color of black). If the average pixel value for the content is closer to 255, this may provide an indication that the content is lighter (e.g., closer to the color of white). As described in more detail elsewhere herein, the device 110 may use the average pixel value for the content to adjust the brightness value used to display the content in accordance with the calibrated brightness setting for the user.

In some other examples, the metric may be a minimum pixel value associated with the content. As another example, the metric may be a maximum pixel value associated with the content. In some aspects, the metric may be based at least in part on pixel values within a region of interest associated with the content. The region of interest may be a subset or an area of the display screen. For example, the region of interest may be an area in which a user typically focuses (e.g., the center of the display screen) or an area in which movement or action is taking place within the content (e.g., an area in which a character or avatar is moving as displayed by the display screen or an area in which action is taking place in the content as displayed by the display screen). For example, the metric may be an average pixel value within the region of interest. As another example, the metric may be a local maximum pixel value within the region of interest. As another example, the metric may be a local minimum pixel value within the region of interest.

Figure 3D:
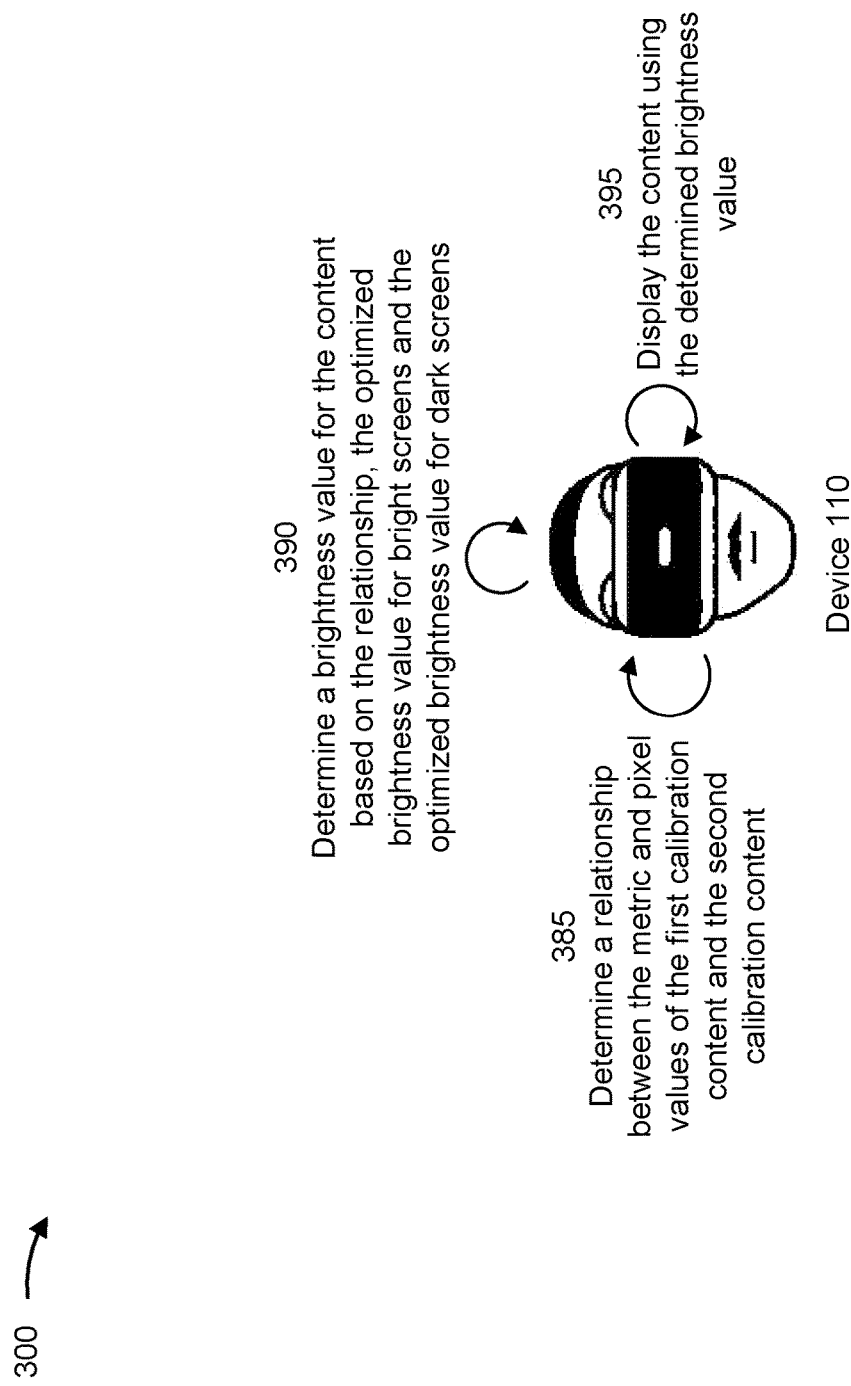

As shown in FIG. 3D, and by reference number 385, the device 110 may determine a relationship between the metric of the content to be displayed, a first pixel value of the first calibration content 315 (e.g., of the background of the first calibration content 315), and a second pixel value of the second calibration content 345 (e.g., of the background of the second calibration content 345). For example, the first calibration content 315 may be associated with a pixel value of 255 or (255, 255, 255) because the background of the first calibration content 315 may be approximately the color white. Similarly, the second calibration content 345 may be associated with a pixel value of 0 or (0, 0, 0) because the background of the second calibration content 345 may be approximately the color black. The device 110 may determine a relationship between the metric and the pixel values of 0 (or (0, 0, 0)) and 255 (or (255, 255, 255)). In some aspects, the relationship may be a linear relationship. In some aspects, the relationship may be a ratio of the metric to the first pixel value and/or the second pixel value. The relationship may provide an indication as to whether the metric is closer to the first pixel value or the second pixel value (e.g., and/or a measure of the closeness).

More generally, the device 110 may determine a relationship between a value of a specific metric (function) calculated for one or more content frames as described above (e.g., based on an average pixel value) and corresponding values of the same specific metric (function) calculated for the first and the second calibration contents. In other words, the same metric may be applied to respective frames of the content to be displayed and the first and second calibration contents to establish a relationship between the respective (perceived) brightness when using the same (e.g., fixed) brightness setting of the display. In the context of the above described calibration of the range of brightness settings using bright and dark content frames as calibration frames, this relationship between the metric value of the content to be displayed and the metric values of the calibration frames may be used to adjust the brightness setting of the display for displaying the content. The device 110 may determine a relationship between the metric (value) of the content to be displayed and the metric values of the first and second calibration contents. In some aspects, the relationship may be a linear relationship. In some aspects, the relationship may be a ratio of the metric (value) of the content to be displayed to the metric (value) of the first calibration content and/or the metric (value) of the second calibration content.

The relationship may provide an indication as to whether the (perceived) brightness of the content to be displayed is closer to the first calibration content or the second calibration content.

As shown by reference number 390, the device 110 may determine a brightness value/setting (e.g., a luminance of the display) to be used to display the content based at least in part on the relationship, the first calibrated brightness value for the first calibration content, e.g., bright content (e.g., n nits) or a particular color, and the second calibrated brightness value for the second calibration content, e.g., dark content (e.g., p nits) or another particular color. In other words, the device 110 may determine the brightness setting of the display for displaying the content based at least in part on a first brightness setting of the display optimized for the user for bright content (e.g., the first calibrated brightness value calibrated using the first calibration content 315), a second brightness setting of the display optimized for the user for dark content (e.g., the second calibrated brightness value calibrated using the second calibration content 345), and the relationship.

For example, if the relationship is a linear relationship, the first calibrated brightness value (e.g., n nits) and the first pixel value or metric value (e.g., 255) associated with the first calibration content 315 may provide a first data point and the second calibrated brightness value (e.g., p nits) and the second pixel value or metric value (e.g., 0) associated with the second calibration content 345 may provide a second data point. The first data point and the second data point may be used to define the linear relationship. The device 110 may use the linear relationship defined by the first data point and the second data point and the average pixel value or metric value of the content being displayed or to be displayed by the device 110 to identify the brightness value/setting (e.g., the luminance) to be used to display the content. The device 110 may use the first data point and the second data point and the average pixel value or metric value of the content being displayed or to be displayed by the device 110 to identify the brightness value/setting (e.g., the luminance) to be used to display the content using other relationships in a similar manner (e.g., the relationship may not be linear in some cases). In some examples, the relationship may be steeper than a purely linear relationship near the first and second data points and may be flatter in the remainder of the range between the two data points. Such a relationship or similar relationships may be used to increase a sensitivity of the change of a brightness value/setting for content with metric values near (e.g., within a margin from) the bounds of the metric value range (e.g., limits of the metric scale) for approximately black and approximately white content. By applying such a non-linear relationship, unnecessary changes to the brightness setting of a display may be avoided for content with intermediate brightness levels that will generally not strain a user's eyes while a significant improvement in brightness perception can be achieved for "very dark" and "very bright" content.

In this way, the device 110 may be enabled to determine the adjusted brightness value/setting of the display based at least in part on the metric (value) associated with the content being displayed or to be displayed by the device 110 and the calibrated brightness setting and without measuring a pupil size of the user after calibrating the brightness setting. In other words, the device 110 may adjust the brightness value/setting used by the device 110 to display content without requiring additional measurements of the pupil size of the user while the user is viewing the content. This may conserve processing resources, memory resources, and/or time that would have otherwise been used to measure the pupil size of the user while the user is viewing the content to facilitate the determination of the adjusted brightness value/setting of the display.

As shown by reference number 395, the device 110 may display the content using the determined brightness value/setting for the content. For example, the device 110 may set a brightness value/setting used to display the content using the adjusted brightness value/setting of the display (e.g., that is determined in accordance with the calibrated brightness setting, as described above). As a result, the device 110 may be enabled to automatically adjust the brightness value/setting used to display content to the user in accordance with a brightness setting that is calibrated for the user using pupil measurements of the user. This may conserve processing and/or memory resources that would have otherwise been used by a user manually adjusting the brightness of the display screen of the device 110. Additionally, this may improve a user experience by personalizing the automatic brightness determinations made by the device 110 to a given user. In some examples, the device 110 may use one of the first and second calibrated brightness values or a value between the first and second calibrated brightness values as the brightness value for displaying the content, in which case the determination of the metric of the content can be omitted, and thus processing and/or memory resources can be further conserved.

In some aspects, the device 110 may periodically determine whether the brightness setting is correctly calibrated for the user. For example, the device 110 may display the content using the adjusted brightness value/setting for the display screen. The device 110 may measure a pupil size of the user, after displaying the content using the adjusted display brightness value/setting, to confirm whether the adjusted display brightness is correctly calibrated for the user. For example, the device 110 may determine whether the brightness setting is accurate for the user based at least in part on the pupil size of the user after displaying the content, a first target pupil size (e.g., that is calibrated based at least in part on the first calibration content 315, such as x millimeters), and a second target pupil size (e.g., that is calibrated based at least in part on the second calibration content 345, such as y millimeters). For example, the device 110 may determine an expected pupil size for the user when using the adjusted display brightness value/setting for the content based at least in part on the first target pupil size and the second target pupil size. For example, the device 110 may determine an expected pupil size for the user using a linear relationship defined by a first data point (e.g., of the first target pupil size and the first calibrated brightness value) and a second data point (e.g., of the second target pupil size and the second calibrated brightness value). The device 110 may use the brightness value used to display the content and the linear relationship to determine the expected pupil size.

The device 110 may determine whether the brightness setting is accurate for the user based at least in part on comparing the measured pupil size of the user (e.g., when viewing the content) to the expected pupil size. If a difference between the measured pupil size of the user and the expected pupil size of the user satisfies, e.g., is smaller than, a threshold, then the device 110 may determine that the brightness setting is accurate (e.g., is correctly calibrated) for the user. If the difference between the measured pupil size of the user and the expected pupil size of the user does not satisfy the threshold, then the device 110 may determine that the brightness setting is not accurate (e.g., is not correctly calibrated) for the user. In such examples, the device 110 may re-calibrate the brightness setting (e.g., in a similar manner as described in more detail elsewhere herein) based at least in part on determining that the brightness setting is not accurate. Additionally, or alternatively, the device 110 may refrain from adjusting the brightness value used by the device 110 in accordance with the brightness setting based at least in part on determining that the brightness setting is not accurate. This may ensure that the device 110 does not adjust the brightness value/setting of the display screen using an inaccurate calibration, thereby conserving processing resources that would have otherwise been used to adjust the brightness of the display screen using the inaccurate calibration and/or improving a user experience.

As indicated above, FIGS. 3A-3D are provided as an example. Other examples may differ from what is described with respect to FIGS. 3A-3D.

FIG. 4 is a flowchart of an example process 400 associated with personalized display brightness based on pupil size. In some implementations, one or more process blocks of FIG. 4 are performed by a device (e.g., the device 110). In some implementations, one or more process blocks of FIG. 4 are performed by another device or a group of devices separate from or including the device, such as a server device (e.g., the server device 120) and/or a communication device (e.g., the communication device 130). Additionally, or alternatively, one or more process blocks of FIG. 4 may be performed by one or more components of device 200, such as processor 210, memory 215, storage component 220, input component 225, output component 230, communication interface 235 and/or sensor 240.

As shown in FIG. 4, process 400 may include determining a first calibrated brightness value for a display screen based at least in part on: displaying first calibration content; adjusting a first brightness value of the display until a first measured pupil size of a user of the display matches a first target pupil size, wherein the first calibrated brightness value is based at least in part on the first brightness value of the display when the first measured pupil size of the user matches the first target pupil size (block 410). For example, the device may determine a first calibrated brightness value for a display screen based at least in part on: displaying first calibration content; adjusting a first brightness value of the display until a first measured pupil size of a user of the display matches a first target pupil size, wherein the first calibrated brightness value is based at least in part on the first brightness value of the display when the first measured pupil size of the user matches the first target pupil size, as described above.

As further shown in FIG. 4, process 400 may include determining a second calibrated brightness value for the display based at least in part on: displaying second calibration content; adjusting a second brightness value of the display until a second measured pupil size of the user matches a second target pupil size, wherein the second calibrated brightness value is based at least in part on the second brightness value of the display when the second measured pupil size of the user matches the second target pupil size (block 420). For example, the device may determine a second calibrated brightness value for the display based at least in part on: displaying second calibration content; adjusting a second brightness value of the display until a second measured pupil size of the user matches a second target pupil size, wherein the second calibrated brightness value is based at least in part on the second brightness value of the display when the second measured pupil size of the user matches the second target pupil size, as described above.

As further shown in FIG. 4, process 400 may optionally include displaying content (block 430). For example, the device may display content, as described above.

As further shown in FIG. 4, process 400 may include a metric value for content to be displayed based upon pixel values of the content (block 440). For example, the device may calculate a metric value for content to be displayed based upon pixel values of the content, as described above.

As further shown in FIG. 4, process 400 may include adjusting a brightness value of the display based at least in part on the first calibrated brightness value, the second calibrated brightness value, and the metric value (block 450). For example, the device may adjust a brightness value of the display based at least in part on the first calibrated brightness value, the second calibrated brightness value, and the metric value, as described above.

Process 400 may include additional aspects, such as any single aspect or any combination of aspects described below and/or in connection with one or more other processes described elsewhere herein, such as in connection with FIGS. 5 and 6.

In a first aspect, adjusting the first brightness value of the display until the first measured pupil size of the user matches the first target pupil size includes repeatedly adjusting the first brightness value of the display while the first calibration content is displayed, and measuring a first pupil size of the user after each adjustment of the first brightness value.

In a second aspect, alone or in combination with the first aspect, process 400 includes a user input indicating a modification to at least one of the first calibrated brightness value or the second calibrated brightness value; and adjusting the at least one of the first calibrated brightness value or the second calibrated brightness value based at least in part on the user input.

In a third aspect, alone or in combination with one or more of the first and second aspects, the first calibration content includes a first one or more calibration frames with a first background having a first pixel value, with a first animation having a second pixel value, and the second calibration screen includes a second background having a third pixel value with a second animation having a fourth pixel value.

In a fourth aspect, alone or in combination with one or more of the first through third aspects, the first pixel value is greater than the third pixel value.

In a fifth aspect, alone or in combination with one or more of the first through fourth aspects, calculating the metric value for the content to be displayed includes calculating, for one or more frames of the content, a frame metric value based on respective pixel values of the one or more frames, and calculating the metric value for the content to be displayed based on an average of the frame metric values of the one or more frames.

In a sixth aspect, alone or in combination with one or more of the first through fifth aspects, adjusting the brightness value includes calculating a first metric value for the first calibration content and a second metric value for the second calibration content; determining a relationship between the metric value for the content to be displayed, the first metric value for the first calibration content, and the second metric value for the second calibration content; and determining the brightness value of the display for displaying the content based on the first calibrated brightness value, the second calibrated brightness value, and the relationship.

In a seventh aspect, alone or in combination with one or more of the first through sixth aspects, process 400 includes displaying the content using the adjusted display brightness for the content.

In an eighth aspect, alone or in combination with one or more of the first through seventh aspects, process 400 includes determining that the first brightness value and the second brightness value of the display can be calibrated and adjusted using a pupil size of the user based at least in part on a dilation time associated with a dilation of a pupil of the user.

In a ninth aspect, alone or in combination with one or more of the first through eighth aspects, process 400 includes the content using the adjusted brightness value, and measuring a pupil size of the user, after displaying the content using the adjusted brightness value, to confirm whether the adjusted brightness value is correctly calibrated for the user.

Although FIG. 4 shows example blocks of process 400, in some implementations, process 400 includes additional blocks, fewer blocks, different blocks, or differently arranged blocks than those depicted in FIG. 4. Additionally, or alternatively, two or more of the blocks of process 400 may be performed in parallel.

Figure 5:
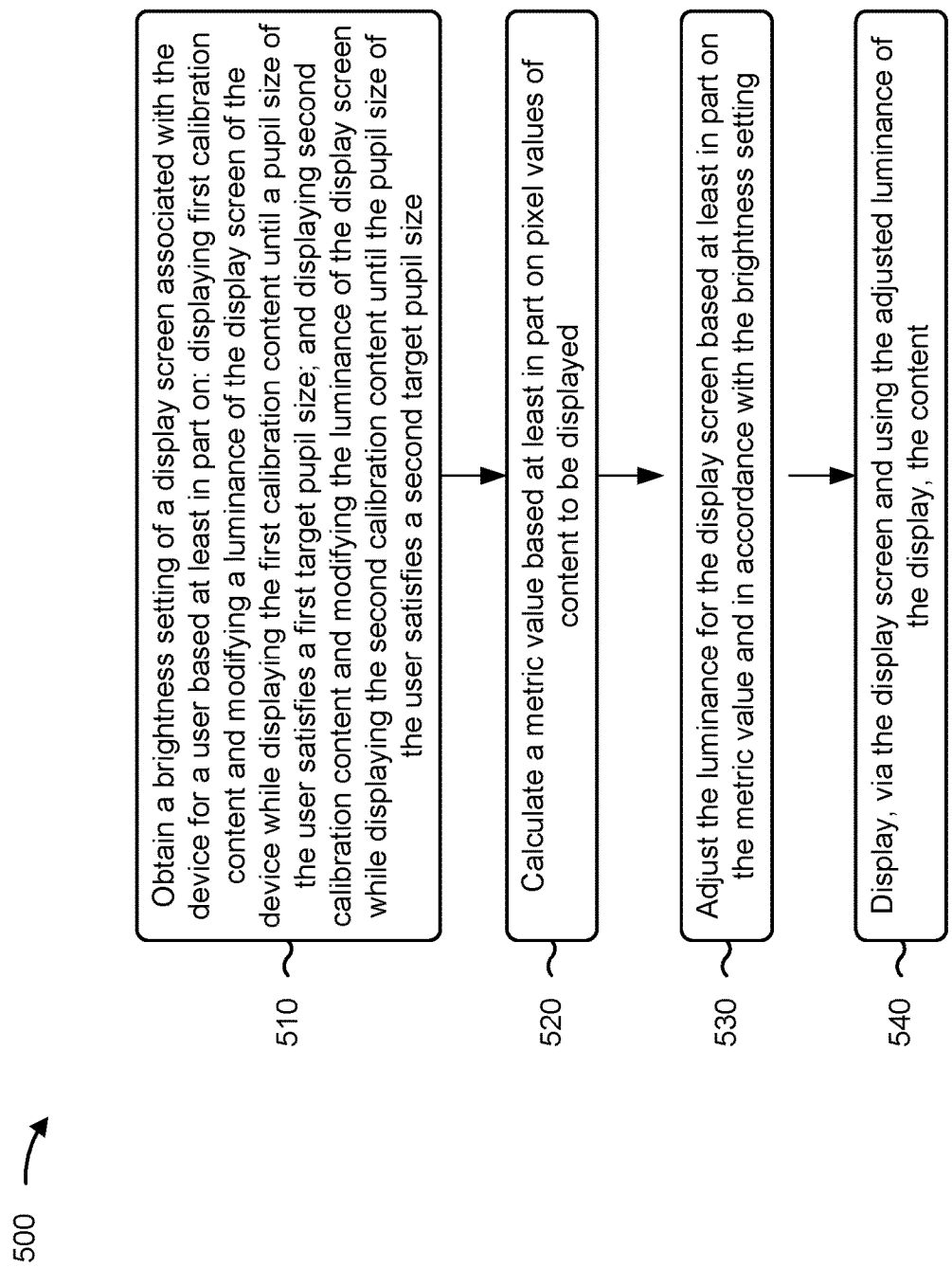

FIG. 5 is a flowchart of an example process 500 associated with personalized display brightness based on pupil size. In some implementations, one or more process blocks of FIG. 5 are performed by a device (e.g., the device 110). In some implementations, one or more process blocks of FIG. 4 are performed by another device or a group of devices separate from or including the device, such as a server device (e.g., the server device 120) and/or a communication device (e.g., the communication device 130). Additionally, or alternatively, one or more process blocks of FIG. 4 may be performed by one or more components of device 200, such as processor 210, memory 215, storage component 220, input component 225, output component 230, communication interface 235 and/or sensor 240.

As shown in FIG. 5, process 500 may include obtaining a brightness setting of a display screen associated with the device for a user based at least in part on: displaying first calibration content and modifying a luminance of the display screen of the device while displaying the first calibration content until a pupil size of the user satisfies a first target pupil size; and displaying second calibration content and modifying the luminance of the display screen while displaying the second calibration content until the pupil size of the user satisfies a second target pupil size (block 510). For example, the device may obtain a brightness setting of a display screen associated with the device for a user based at least in part on: displaying first calibration content and modifying a luminance of the display screen of the device while displaying the first calibration content until a pupil size of the user satisfies a first target pupil size; and displaying second calibration content and modifying the luminance of the display screen while displaying the second calibration content until the pupil size of the user satisfies a second target pupil size, as described above.

As further shown in FIG. 5, process 500 may include calculating a metric value based at least in part on pixel values of content to be displayed (block 520). For example, the device may calculate a metric value based at least in part on pixel values of content to be displayed, as described above.

As further shown in FIG. 5, process 500 may include adjusting the luminance for the display screen based at least in part on the metric value and in accordance with the brightness setting (block 530). For example, the device may adjust the luminance for the display screen based at least in part on the metric value and in accordance with the brightness setting, as described above.

As further shown in FIG. 5, process 500 may include displaying, via the display screen and using the adjusted luminance, the content (block 540). For example, the device may display, via the display screen and using the adjusted luminance, the content, as described above.

Process 500 may include additional aspects, such as any single aspect or any combination of aspects described below and/or in connection with one or more other processes described elsewhere herein, such as in connection with FIGS. 4 and 6.

In a first aspect, the brightness setting includes a first pupil size and a first luminance of the display optimized for the user for the first calibration screen, and a second pupil size and a second luminance of the display optimized for the user for the second calibration screen.

In a second aspect, alone or in combination with the first aspect, adjusting the luminance includes determining a relationship between the metric value, a first pixel value associated with the first calibration content, and a second pixel value associated with the second calibration content, and determining the luminance of the display for the display screen based at least in part on the first luminance of the display, the second luminance of the display, and the relationship.

In a third aspect, alone or in combination with one or more of the first and second aspects, process 500 includes measuring the pupil size of the user after displaying the content using the adjusted luminance, determining whether the brightness setting is accurate for the user based at least in part on the pupil size of the user after displaying the content, the first pupil size, and the second pupil size, and re-calibrating the brightness setting based at least in part on determining that the brightness setting is not accurate.

In a fourth aspect, alone or in combination with one or more of the first through third aspects, process 500 includes displaying the first calibration content including a first background having a first pixel value and a first animation having a second pixel value, and displaying the second calibration content including a second background having a third pixel value and a second animation having a fourth pixel value.

In a fifth aspect, alone or in combination with one or more of the first through fourth aspects, process 500 includes receiving a user input indicating an adjustment to at least one of a first luminance calibrated for the first calibration content, or a second luminance calibrated for the second calibration content, wherein the brightness setting is based at least in part on the user input.

In a sixth aspect, alone or in combination with one or more of the first through fifth aspects, process 500 includes displaying the first calibration content using a first luminance for a first interval of time, measuring the pupil size of the user after the first interval of time, and displaying the first calibration content using a second luminance for a second interval of time based at least in part on a difference between the pupil size of the user after the first interval and the first target pupil size not satisfying a threshold.

In a seventh aspect, alone or in combination with one or more of the first through sixth aspects, calculating the metric value includes calculating, for a set of pixels of a frame of the content, a set of pixel values based at least in part on RGB triplet values associated with the set of pixels, calculating, for the frame, a frame pixel value based at least in part on the set of pixel values, and calculating the metric value based at least in part on averaging frame pixel values, including the frame pixel value, of one or more frames, including the frame, of the content.

In an eighth aspect, alone or in combination with one or more of the first through seventh aspects, process 500 includes determining whether the device is enabled to calibrate the brightness setting using the pupil size of the user based at least in part on comparing an amount of time that a pupil of the user takes to dilate to a dilation time.

In a ninth aspect, alone or in combination with one or more of the first through eighth aspects, the device includes at least one of a virtual reality device, an augmented reality device, a head mounted display device, or smart eyeglasses.

In a tenth aspect, alone or in combination with one or more of the first through ninth aspects, process 500 includes storing the brightness setting as being associated with a user profile associated with the user; receiving a credential associated with the user profile; and loading the brightness setting for a session associated with the user profile based on authenticating the credential.

In an eleventh aspect, alone or in combination with one or more of the first through tenth aspects, the metric includes at least one of: a statistical average of the pixel values of the content, a first average pixel value of the content, a local maximum of pixel values of the content in a region of interest, a local minimum of the pixel values of the content in the region of interest, or a second average pixel value of the pixel values of the content in the region of interest.

In a twelfth aspect, alone or in combination with one or more of the first through eleventh aspects, obtaining the brightness setting is based at least in part on detecting a calibration event.

Although FIG. 5 shows example blocks of process 500, in some implementations, process 500 includes additional blocks, fewer blocks, different blocks, or differently arranged blocks than those depicted in FIG. 5. Additionally, or alternatively, two or more of the blocks of process 500 may be performed in parallel.

Figure 6:
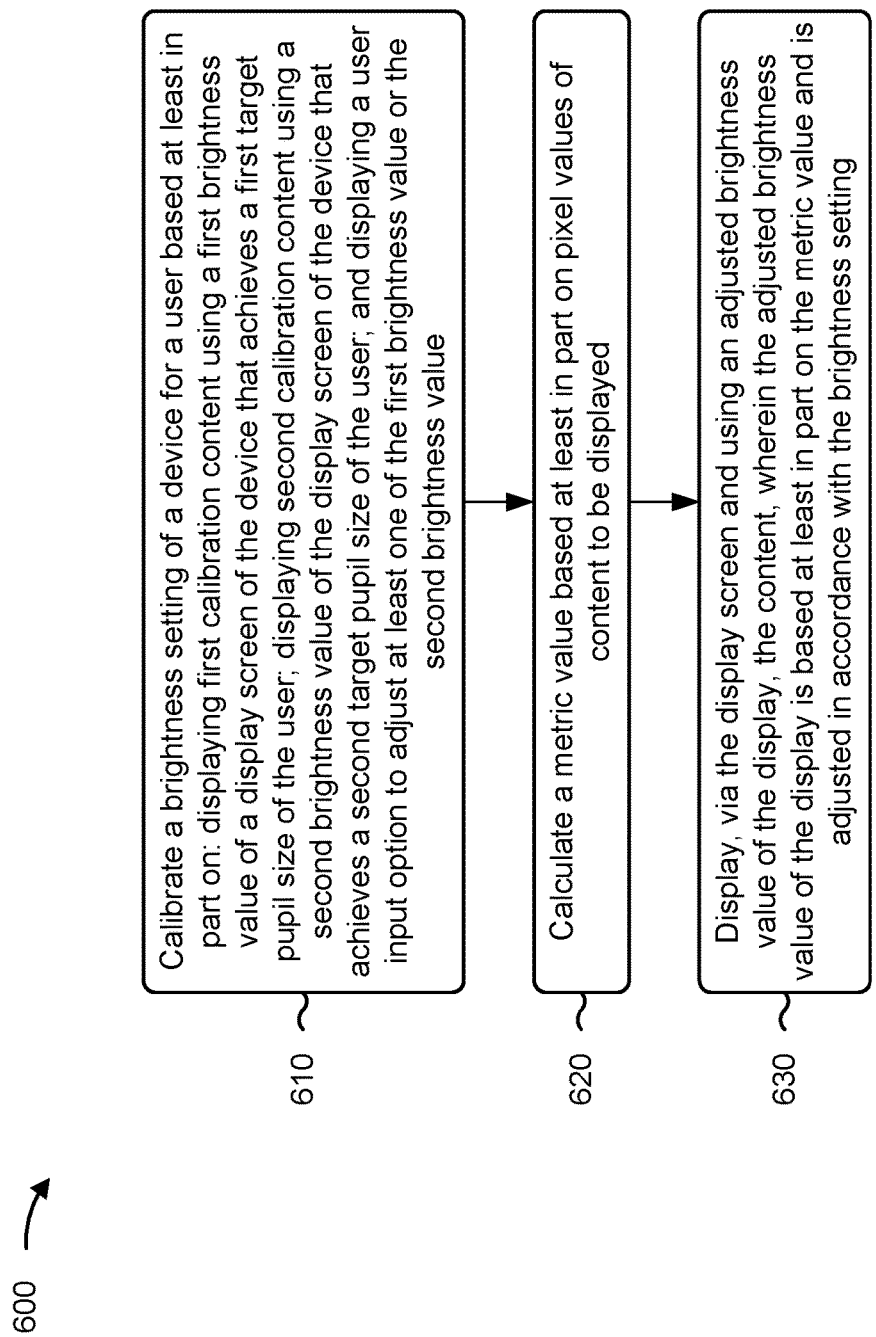

FIG. 6 is a flowchart of an example process 600 associated with personalized display brightness based on pupil size. In some implementations, one or more process blocks of FIG. 6 are performed by a device (e.g., the device 110). In some implementations, one or more process blocks of FIG. 4 are performed by another device or a group of devices separate from or including the device, such as a server device (e.g., the server device 120) and/or a communication device (e.g., the communication device 130). Additionally, or alternatively, one or more process blocks of FIG. 4 may be performed by one or more components of device 200, such as processor 210, memory 215, storage component 220, input component 225, output component 230, communication interface 235 and/or sensor 240.

As shown in FIG. 6, process 600 may include calibrating a brightness setting of the device for a user based at least in part on: displaying first calibration content using a first brightness value of a display screen of the device that achieves a first target pupil size of the user; displaying second calibration content using a second brightness value of the display screen of the device that achieves a second target pupil size of the user; and displaying a user input option to adjust at least one of the first brightness value or the second brightness value (block 610). For example, the device may calibrate a brightness setting of the device for a user based at least in part on: displaying first calibration content using a first brightness value of a display screen of the device that achieves a first target pupil size of the user; displaying second calibration content using a second brightness value of the display screen of the device that achieves a second target pupil size of the user; and displaying a user input option to adjust at least one of the first brightness value or the second brightness value, as described above.

As further shown in FIG. 6, process 600 may include calculating a metric value based at least in part on pixel values of content to be displayed (block 620). For example, the device may calculate a metric value based at least in part on pixel values of content to be displayed, as described above.

As further shown in FIG. 6, process 600 may include displaying, via the display screen and using an adjusted brightness value of the display, the content, wherein the adjusted brightness value of the display is based at least in part on the metric value and is adjusted in accordance with the brightness setting (block 630). For example, the device may display, via the display screen and using an adjusted brightness value of the display, the content, wherein the adjusted brightness value of the display is based at least in part on the metric value and is adjusted in accordance with the brightness setting, as described above.

Process 600 may include additional aspects, such as any single aspect or any combination of aspects described below and/or in connection with one or more other processes described elsewhere herein, such as in connection with FIGS. 4 and 5.

In a first aspect, wherein the brightness setting includes a first pupil size and the first brightness value optimized for the user for the first calibration content, and a second pupil size and the second brightness value for the user for the second calibration content.

In a second aspect, alone or in combination with the first aspect, process 600 includes determining a relationship between the metric value, a first pixel value associated with the first calibration content, and a second pixel value associated with the second calibration content; and determining the adjusted brightness value based at least in part on the first brightness value, the second brightness value, and the relationship.

In a third aspect, alone or in combination with one or more of the first and second aspects, process 600 includes displaying the first calibration screen including a first background having a first pixel value that approximately corresponds to white, and displaying the second calibration screen including a second background having a second pixel value that approximately corresponds to black.

In a fourth aspect, alone or in combination with one or more of the first through third aspects, the first target pupil size is an optimized pupil size for bright light environments, and wherein the second target pupil size is an optimized pupil size for dark environments.

In a fifth aspect, alone or in combination with one or more of the first through fourth aspects, process 600 includes determining the adjusted brightness value based at least in part on the metric value and the brightness setting and without measuring a pupil size of the user after calibrating the brightness setting.

Although FIG. 6 shows example blocks of process 600, in some implementations, process 600 includes additional blocks, fewer blocks, different blocks, or differently arranged blocks than those depicted in FIG. 6. Additionally, or alternatively, two or more of the blocks of process 600 may be performed in parallel.

Figure 7:
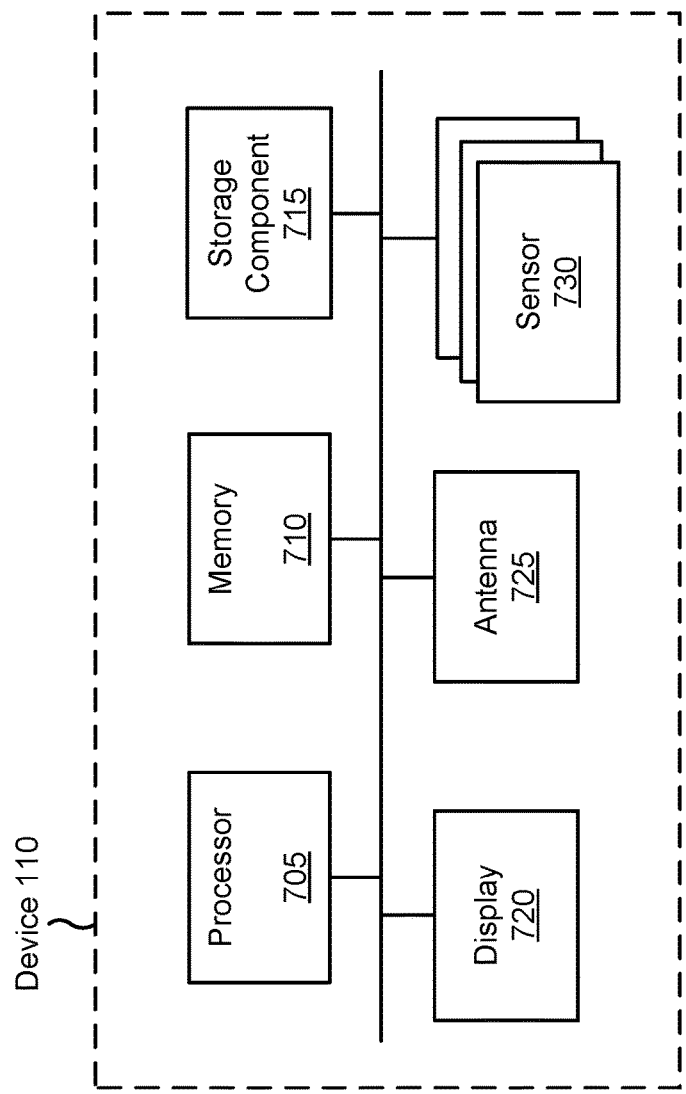
FIG. 7 is a diagram illustrating example components of a device, in accordance with the present disclosure.

FIG. 7 is a diagram illustrating example components 700 of the device 110, in accordance with the present disclosure. In some aspects, the device 110 may include one or more of the example components 700. As shown in FIG. 7, example components 700 may include a processor 705, a memory 710, a storage component 715, a display 720, an antenna 725, and/or a sensor 730.

In some aspects, the device 110 may include a bus that includes a component that permits communication among the components of device 110. The processor 705 may be, may include, or may be similar to the processor 210. For example, the processor 705 may implemented in hardware, firmware, or a combination of hardware and software. The processor 705 may be a CPU, a GPU, an APU, a microprocessor, a microcontroller, a DSP, an FPGA, an ASIC, or another type of processing component. The processor 705 may include one or more processors capable of being programmed to perform a function.

The memory 710 may be, may include, or may be similar to the memory 215. For example, the memory 710 may include a RAM, a ROM, and/or another type of dynamic or static storage device (e.g., a flash memory, a magnetic memory, and/or an optical memory) that stores information and/or instructions for use by processor 705.

The storage component 715 may be, may include, or may be similar to the storage component 220. For example, the storage component 715 may store information and/or software related to the operation and use of the device 110. For example, the storage component 715 may include a hard disk (e.g., a magnetic disk, an optical disk, a magneto-optic disk, and/or a solid state disk), a flash memory device, a CD, a DVD, a cartridge, a magnetic tape, and/or another type of non-transitory computer-readable medium, along with a corresponding drive.

The display 720 may include one or more components that provide output information from device 110. The display 720 may be any display capable of displaying content associated with the device 110, as described in more detail elsewhere herein. The display 720 may also be referred to herein as a display screen. The display 720 may be any display and/or screen associated with an adjustable brightness or luminance setting. For example, the display 720 may include a screen (e.g., a display screen) that is associated with an adjustable brightness. In some aspects, the display 720 may include a backlight. In some other aspects, the display 720 may not include a backlight. In some aspects, the display 720 may be, or may include, a human-machine interface and/or a graphical user interface. The display 720 may include an LCD display, an LED display, an LED backlit LCD display, a thin-film transistor (TFT) LCD display, a quantum dot (QD) LED display, an OLED display, an active-matrix OLED (AMOLED) display, a retinal projection display, a vacuum fluorescent display, an electroluminescent display, or a plasma display panel (PDP) display, among other examples. In some aspects, the display 720 may be, may include, or may be similar to the input component 225 and/or the output component 230.

The device 110 may include one or more antennas 725. An antenna 725 may be a component capable of receiving and/or transmitting signals (e.g., wireless communication signals). One or more antennas 725 may include, or may be included within, one or more antenna panels, one or more antenna groups, one or more sets of antenna elements, and/or one or more antenna arrays, among other examples. An antenna panel, an antenna group, a set of antenna elements, and/or an antenna array may include one or more antenna elements (within a single housing or multiple housings), a set of coplanar antenna elements, a set of non-coplanar antenna elements, and/or one or more antenna elements coupled to one or more transmission and/or reception components. For example, an antenna 725 may receive a signal and provide the signal to another component of the device 110, such as the processor 705. As another example, the antenna 725 may receive instructions from a component of the device 110, such as the processor 705, to transmit a signal and may transmit the signal in accordance with the instructions. In some aspects, the device 110 may receive instructions from another device, such as the server device 120 or the communication device 130, to perform one or more operations described herein via a signal received by an antenna 725.

The sensor 730 may be, may include, or may be similar to the sensor 240. For example, the sensor 730 may include one or more wired or wireless devices capable of detecting and/or measuring a pupil size of the user. For example, the sensor 730 may include a camera, an NIR camera, an optical sensor, an optical camera, an eye tracking sensor, a pupilometer, or a similar type of device. As another example, the sensor 730 may include one or more wired or wireless devices capable of measuring a brightness value of the display 720.

The device 110 may perform one or more processes described herein. The device 110 may perform these processes based on the processor 705 executing software instructions stored by a non-transitory computer-readable medium, such as the memory 710 and/or the storage component 715. Software instructions may be read into the memory 710 and/or the storage component 715 from another computer-readable medium or from another device. When executed, software instructions stored in the memory 710 and/or the storage component 715 may cause the processor 705 to perform one or more processes described herein. Additionally, or alternatively, hardwired circuitry may be used in place of or in combination with software instructions to perform one or more processes described herein. Thus, aspects described herein are not limited to any specific combination of hardware circuitry and software.

The number and arrangement of components shown in FIG. 7 are provided as an example. In practice, the example components 700 may include additional components, fewer components, different components, or differently arranged components than those shown in FIG. 7. Additionally, or alternatively, a set of components (e.g., one or more components) of the example components 700 may perform one or more functions described as being performed by another set of components of the example components 700.

Figure 8:
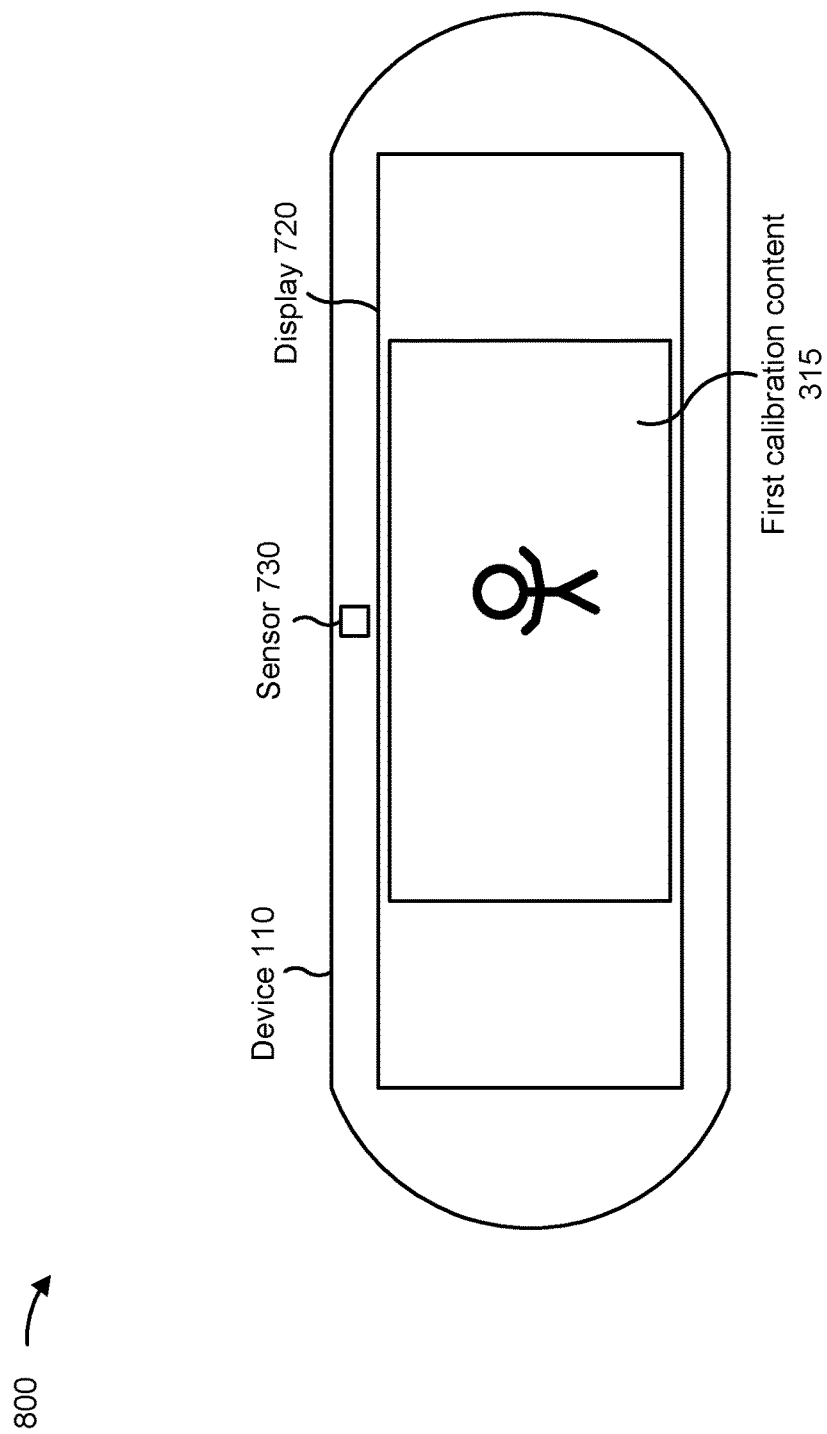
FIG. 8 is a diagram illustrating

FIG. 8 is a diagram illustrating an example 800 of a display and a sensor of the device 110, in accordance with the present disclosure. For example, the display may be the display 720 and the sensor may be the sensor 730. Example 800 depicts the device 110 from a perspective of a user viewing the display 720 of the device 110. For example, in examples where the device 110 is a headset or a wearable device, FIG. 8 may depict view of the device 110 from a perspective of a user wearing, or viewing content via, the device 110.

As described elsewhere herein, the display 720 may be capable of displaying content. The display 720 is depicted displaying the first calibration content 315 in FIG. 8 as an example. The display 720 may display other content, as described herein, in a similar manner. The display 720 may be configured on or in the device 110 so as to be viewed by a user.

The device 110 may include the sensor 730. The sensor 730 may be configured or positioned on or in the device 110 to enable the sensor 730 to measure and/or track one or more eyes of a user viewing the display 720. For example, as shown in FIG. 8, the sensor 730 may be positioned proximate to the display 720 and/or may be configured to face a direction toward a user who is viewing the display 720. This may enable the sensor 730 to measure, track, or otherwise sense a pupil size of the user. The device 110 may use pupil measurements, performed by the sensor 730, to adjust and/or calibrate a brightness setting of the display 720, as described in more detail elsewhere herein.

The number and arrangement of components shown in FIG. 8 are provided as an example. In practice, example 800 may include additional components, fewer components, different components, or differently arranged components than those shown in FIG. 8. Additionally, or alternatively, a set of components (e.g., one or more components) of the device 110 may perform one or more functions described as being performed by another set of components of the example 800.

The following provides an overview of some Aspects of the present disclosure:

Aspect 1: A method, comprising: determining, by a device, a first calibrated brightness value for a display screen based at least in part on: displaying, by the device, first calibration content; adjusting, by the device, a first brightness value of the display until a first measured pupil size of a user of the device matches a first target pupil size, wherein the first calibrated brightness value is based at least in part on the first brightness value of the display when the first measured pupil size of the user matches the first target pupil size; determining, by the device, a second calibrated brightness value for the display based at least in part on: displaying, by the device, second calibration content; adjusting, by the device, a second brightness value of the display until a second measured pupil size of the user matches a second target pupil size, wherein the second calibrated brightness value is based at least in part on the second brightness value of the display when the second measured pupil size of the user matches the second target pupil size; calculating, by the device, a metric value for content to be displayed based upon pixel values of the content; and adjusting, by the device, a brightness value of the display based at least in part on the first calibrated brightness value, the second calibrated brightness value, and the metric value.

Aspect 2: The method of Aspect 1, wherein adjusting the first brightness value of the display until the first measured pupil size of the user matches the first target pupil size comprises: repeatedly adjusting the first brightness value of the display while the first calibration content is displayed; and measuring a first pupil size of the user after each adjustment of the first brightness value.

Aspect 3: The method of any of Aspects 1-2, further comprising: receiving a user input indicating a modification to at least one of the first calibrated brightness value or the second calibrated brightness value; and adjusting the at least one of the first calibrated brightness value or the second calibrated brightness value based at least in part on the user input.

Aspect 4: The method of Aspect 3, further comprising: adjusting at least one of the first target pupil size or the second target pupil size based at least in part on the user input.

Aspect 5: The method of any of Aspects 1-4, wherein the first calibration content includes a first one or more calibration frames with a first background having a first pixel value, with a first animation having a second pixel value; and wherein the second calibration screen includes a second background having a third pixel value with a second animation having a fourth pixel value.

Aspect 6: The method of Aspect 5, wherein the first pixel value is greater than the third pixel value.

Aspect 7: The method of any of Aspects 5-6, wherein the first pixel value corresponds to white and the third pixel value corresponds to black.

Aspect 8: The method of any of Aspects 1-7, wherein calculating the metric value for the content to be displayed comprises: calculating, for one or more frames of the content, a frame metric value based on respective pixel values of the one or more frames; and calculating the metric value for the content to be displayed based on an average of the frame metric values of the one or more frames.

Aspect 9: The method of any of Aspects 1-8, wherein adjusting the brightness value comprises: calculating a first metric value for the first calibration content and a second metric value for the second calibration content; determining a relationship between the metric value for the content to be displayed, the first metric value for the first calibration content, and the second metric value for the second calibration content; and determining the brightness value of the display for displaying the content based on the first calibrated brightness value, the second calibrated brightness value, and the relationship.

Aspect 10: The method of any of Aspects 1-9, further comprising: displaying the content using the adjusted brightness value.

Aspect 11: The method of any of Aspects 1-10, further comprising: determining that the first brightness value and the second brightness value of the display can be calibrated and adjusted using a pupil size of the user based at least in part on a dilation time associated with a dilation of a pupil of the user.

Aspect 12: The method of any of Aspects 1-11, further comprising: displaying the content using the adjusted brightness value; and measuring a pupil size of the user, after displaying the content using the adjusted brightness value, to confirm whether the adjusted brightness value is correctly calibrated for the user.

Aspect 13: The method of any of Aspects 1-12, wherein calculating the metric value for the content to be displayed comprises calculating a statistical average of the pixel values of one or more frames of the content to be displayed.

Aspect 14: The method of Aspect 13, wherein the pixel values comprise at least one of one color component value, two color component values, three color component values, a luminance or luma component value, or a weighted average of color component values.

Aspect 15: The method of any of Aspects 1-14, wherein the first calibration content has a higher average luminance than the second calibration content.

Aspect 16: The method of any of Aspects 1-15, wherein the first calibration content is biased towards or has a first color among a red color, a green color, and a blue color; and wherein the second calibration content is biased towards or has a second color among the red color, the green color, and the blue color.

Aspect 17: The method of any of Aspects 1-16, wherein the first calibrated brightness value is determined for a left-hand screen of a dual screen display and the second calibrated brightness value is determined for a right-hand screen of the dual screen display; wherein the first target pupil size and the first measured pupil size are with respect to a left-hand eye of the user and the second target pupil size and the second measurement pupil size are with respect to a right-hand eye of the user; and wherein the second calibration content is identical to the first calibration content.

Aspect 18: The method of any of Aspects 1-17, further comprising: identifying at least one of the first calibration content or the second calibration content from a plurality of content to be displayed by the device.

Aspect 19: The method of any of Aspects 1-18, wherein the metric value includes at least one of: a statistical average of the pixel values of the content, a first average pixel value of the content, a local maximum of pixel values of the content in a region of interest, a local minimum of the pixel values of the content in the region of interest, or a second average pixel value of the content in the region of interest.

Aspect 20: A method, comprising: obtaining, by a device, a brightness setting of a display screen associated with the device for a user based at least in part on: displaying first calibration content and modifying a luminance of the display screen of the device while displaying the first calibration content until a pupil size of the user satisfies a first target pupil size; and displaying second calibration content and modifying the luminance of the display screen while displaying the second calibration content until the pupil size of the user satisfies a second target pupil size; calculating, by the device, a metric value based at least in part on pixel values of content to be displayed; adjusting, by the device, the luminance for the display screen based at least in part on the metric value and in accordance with the brightness setting; and displaying, by the device via the display screen and using the adjusted luminance of the display, the content.

Aspect 21: The method of Aspect 20, wherein the brightness setting includes a first pupil size and a first luminance of the display screen optimized for the user for the first calibration content, and a second pupil size and a second luminance of the display screen optimized for the user for the second calibration content.

Aspect 22: The method of Aspect 21, wherein adjusting the luminance for the display screen comprises: determining a relationship between the metric value, a first pixel value associated with the first calibration content, and a second pixel value associated with the second calibration content; and determining the luminance for the display screen based at least in part on the first luminance of the display, the second luminance of the display, and the relationship.

Aspect 23: The method of any of Aspects 21-22, further comprising: measuring the pupil size of the user after displaying the content using the adjusted luminance; determining whether the brightness setting is accurate for the user based at least in part on the pupil size of the user after displaying the content, the first pupil size, and the second pupil size; and re-calibrating the brightness setting based at least in part on determining that the brightness setting is not accurate.

Aspect 24: The method of any of Aspects 20-23, wherein obtaining the brightness setting comprises: displaying the first calibration content including a first background having a first pixel value and a first animation having a second pixel value; and displaying the second calibration content including a second background having a third pixel value and a second animation having a fourth pixel value.

Aspect 25: The method of Aspect 24, wherein the first pixel value corresponds to white, the second pixel value corresponds to a first color other than white, the third pixel value corresponds to black, and the fourth pixel value corresponds to a second color other than black.

Aspect 26: The method of any of Aspects 20-25, wherein obtaining the brightness setting comprises: receiving a user input indicating an adjustment to at least one of: a first luminance of the display screen calibrated for the first calibration content, or a second luminance of the display screen calibrated for the second calibration content, wherein the brightness setting is based at least in part on the user input.

Aspect 27: The method of any of Aspects 20-26, wherein obtaining the brightness setting comprises: displaying the first calibration content using a first luminance of the display screen for a first interval of time; measuring the pupil size of the user after the first interval of time; and displaying the first calibration content using a second luminance of the display screen for a second interval of time based at least in part on a difference between the pupil size of the user after the first interval and the first target pupil size not satisfying a threshold.

Aspect 28: The method of any of Aspects 20-27, wherein calculating the metric value comprises: calculating, for a set of pixels of a frame of the content, a set of pixel values based at least in part on red, green, and blue (RGB) triplet values associated with the set of pixels; calculating, for the frame, a frame pixel value based at least in part on the set of pixel values; and calculating the metric value based at least in part on averaging frame pixel values, including the frame pixel value, of one or more frames, including the frame, of the content.

Aspect 29: The method of any of Aspects 20-28, further comprising: determining whether the device is enabled to calibrate the brightness setting using the pupil size of the user based at least in part on comparing an amount of time that a pupil of the user takes to dilate to a dilation time.

Aspect 30: The method of any of Aspects 20-29, wherein the device includes at least one of: a virtual reality device, an augmented reality device, a head mounted display device, or smart eyeglasses.

Aspect 31: The method of any of Aspects 20-30, further comprising storing the brightness setting as being associated with a user profile associated with the user; receiving a credential associated with the user profile; and loading the brightness setting for a session associated with the user profile based on authenticating the credential.

Aspect 32: The method of any of Aspects 20-31, wherein the metric value includes at least one of: a statistical average of the pixel values of the content, a first average pixel value of the content, a local maximum of pixel values of the content in a region of interest, a local minimum of the pixel values of the content in the region of interest, or a second average pixel value of the pixel values of the content in the region of interest.

Aspect 33: The method of any of Aspects 20-32, wherein calibrating the brightness setting is based at least in part on detecting a calibration event.

Aspect 34: The method of any of Aspects 20-33, wherein the first calibration content has a higher average luminance than the second calibration content.

Aspect 35: The method of any of Aspects 20-34, wherein the first calibration content is biased towards or has a first color among a red color, a green color, and a blue color; and wherein the second calibration content is biased towards or has a second color among the red color, the green color, and the blue color.

Aspect 36: The method of any of Aspects 20-35, wherein the brightness setting is determined for a left-hand screen of a dual screen display for a right-hand screen of the dual screen display; wherein the first target pupil size is with respect to a left-hand eye of the user and the second target pupil size is with respect to a right-hand eye of the user; and wherein the second calibration content is identical to the first calibration content.

Aspect 37: The method of any of Aspects 20-36, further comprising: identifying at least one of the first calibration content or the second calibration content from a plurality of content to be displayed by the device.

Aspect 38: A method, comprising: calibrating, by a device, a brightness setting of the device for a user based at least in part on: displaying, by the device, displaying first calibration content using a first brightness value of a display screen of the device that achieves a first target pupil size of the user; displaying, by the device, second calibration content using a second brightness value of the display screen of the device that achieves a second target pupil size of the user; and displaying, by the device, a user input option to adjust at least one of the first brightness value or the second brightness value; calculating, by the device, a metric value based at least in part on pixel values of content to be displayed; and displaying, by the device via the display screen and using an adjusted brightness value, the content, wherein the adjusted brightness value is based at least in part on the metric value and is adjusted in accordance with the brightness setting.

Aspect 39: The method of Aspect 38, wherein the brightness setting includes a first pupil size and the first brightness value optimized for the user for the first calibration content, and a second pupil size and the second brightness value for the user for the second calibration content.

Aspect 40: The method of Aspect 39, further comprising: determining a relationship between the metric value, a first pixel value associated with the first calibration content, and a second pixel value associated with the second calibration content; and determining the adjusted brightness value based at least in part on the first brightness value, the second brightness value, and the relationship.

Aspect 41: The method of any of Aspects 38-40, wherein calibrating the brightness setting comprises: displaying the first calibration content including a first background having a first pixel value that corresponds to white; and displaying the second calibration content including a second background having a second pixel value that corresponds to black.

Aspect 42: The method of any of Aspects 38-41, wherein the first target pupil size is an optimized pupil size for bright light environments, and wherein the second target pupil size is an optimized pupil size for dark environments.

Aspect 43: The method of any of Aspects 38-42, wherein displaying the content comprises: determining the adjusted brightness value based at least in part on the metric value and the brightness setting and without measuring a pupil size of the user after calibrating the brightness setting.

Aspect 44: An apparatus at a device, comprising a processor; memory coupled with the processor; and instructions stored in the memory and executable by the processor to cause the apparatus to perform the method of one or more of Aspects 1-19, 20-37, and/or 38-43.

Aspect 45: A device, comprising a memory and one or more processors coupled to the memory, the one or more processors configured to perform the method of one or more of Aspects 1-19, 20-37, and/or 38-43.

Aspect 46: An apparatus for wireless communication, comprising at least one means for performing the method of one or more of Aspects 1-19, 20-37, and/or 38-43.

Aspect 47: A non-transitory computer-readable medium storing code, the code comprising instructions executable by a processor to perform the method of one or more of Aspects 1-19, 20-37, and/or 38-43.

Aspect 48: A non-transitory computer-readable medium storing a set of instructions, the set of instructions comprising one or more instructions that, when executed by one or more processors of a device, cause the device to perform the method of one or more of Aspects 1-19, 20-37, and/or 38-43.

The foregoing disclosure provides illustration and description but is not intended to be exhaustive or to limit the aspects to the precise forms disclosed. Modifications and variations may be made in light of the above disclosure or may be acquired from practice of the aspects.

As used herein, the term "component" is intended to be broadly construed as hardware and/or a combination of hardware and software. "Software" shall be construed broadly to mean instructions, instruction sets, code, code segments, program code, programs, subprograms, software modules, applications, software applications, software packages, routines, subroutines, objects, executables, threads of execution, procedures, and/or functions, among other examples, whether referred to as software, firmware, middleware, microcode, hardware description language, or otherwise. As used herein, a "processor" is implemented in hardware and/or a combination of hardware and software. It will be apparent that systems and/or methods described herein may be implemented in different forms of hardware and/or a combination of hardware and software. The actual specialized control hardware or software code used to implement these systems and/or methods is not limiting of the aspects. Thus, the operation and behavior of the systems and/or methods are described herein without reference to specific software code, since those skilled in the art will understand that software and hardware can be designed to implement the systems and/or methods based, at least in part, on the description herein.

As used herein, "satisfying a threshold" may, depending on the context, refer to a value being greater than the threshold, greater than or equal to the threshold, less than the threshold, less than or equal to the threshold, equal to the threshold, not equal to the threshold, or the like.

Even though particular combinations of features are recited in the claims and/or disclosed in the specification, these combinations are not intended to limit the disclosure of various aspects. Many of these features may be combined in ways not specifically recited in the claims and/or disclosed in the specification. The disclosure of various aspects includes each dependent claim in combination with every other claim in the claim set. As used herein, a phrase referring to "at least one of" a list of items refers to any combination of those items, including single members. As an example, "at least one of: a, b, or c" is intended to cover a, b, c, a+b, a+c, b+c, and a+b+c, as well as any combination with multiples of the same element (e.g., a+a, a+a+a, a+a+b, a+a+c, a+b+b, a+c+c, b+b, b+b+b, b+b+c, c+c, and c+c+c, or any other ordering of a, b, and c).

No element, act, or instruction used herein should be construed as critical or essential unless explicitly described as such. Also, as used herein, the articles "a" and "an" are intended to include one or more items and may be used interchangeably with "one or more." Further, as used herein, the article "the" is intended to include one or more items referenced in connection with the article "the" and may be used interchangeably with "the one or more." Furthermore, as used herein, the terms "set" and "group" are intended to include one or more items and may be used interchangeably with "one or more." Where only one item is intended, the phrase "only one" or similar language is used. Also, as used herein, the terms "has," "have," "having," or the like are intended to be open-ended terms that do not limit an element that they modify (e.g., an element "having" A may also have B). Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

What is claimed is:

1. A method, comprising:
determining, by a device, a first calibrated brightness value for a display that is displaying bright content based at least in part on:
  displaying, by the device, first calibration content that includes one or more first calibration frames with a first background that approximately corresponds to white, and
  adjusting, by the device and while the first calibration content is displayed, a first brightness value of the display until a first measured pupil size of a user of the display matches a first target pupil size, wherein the first calibrated brightness value is based at least in part on the first brightness value of the display when the first measured pupil size of the user matches the first target pupil size;
determining, by the device, a second calibrated brightness value for the display that is displaying dark content based at least in part on:
  displaying, by the device, second calibration content that includes one or more second calibration frames with a second background that approximately corresponds to black, and
  adjusting, by the device and while the second calibration content is displayed, a second brightness value of the display until a second measured pupil size of the user matches a second target pupil size, wherein the second calibrated brightness value is based at least in part on the second brightness value of the display when the second measured pupil size of the user matches the second target pupil size;
calculating, by the device, a metric value for content to be displayed based upon pixel values of the content; and
adjusting, by the device, a brightness value of the display based at least in part on the first calibrated brightness value, the second calibrated brightness value, and the metric value.

2. The method of claim 1, wherein adjusting the first brightness value of the display until the first measured pupil size of the user matches the first target pupil size comprises:
repeatedly adjusting the first brightness value of the display while the first calibration content is displayed; and
measuring a first pupil size of the user after each adjustment of the first brightness value.

3. The method of claim 1, further comprising:
receiving a user input indicating a modification to at least one of the first calibrated brightness value or the second calibrated brightness value; and
adjusting the at least one of the first calibrated brightness value or the second calibrated brightness value based at least in part on the user input.

4. The method of claim 1, wherein the one or more first calibration frames include the first background having a first pixel value and a first animation having a second pixel value; and
  wherein the one or more second calibration frames include the second background having a third pixel value and a second animation having a fourth pixel value.

5. The method of claim 4, wherein the first pixel value is greater than the third pixel value.

6. The method of claim 1, wherein calculating the metric value for the content to be displayed comprises:
calculating, for one or more frames of the content, a frame metric value based on respective pixel values of the one or more frames; and
calculating the metric value for the content to be displayed based on an average of the frame metric values of the one or more frames.

7. The method of claim 1, wherein adjusting the brightness value comprises:
calculating a first metric value for the first calibration content and a second metric value for the second calibration content;
determining a relationship between the metric value for the content to be displayed, the first metric value for the first calibration content, and the second metric value for the second calibration content; and
determining the brightness value of the display for displaying the content based on the first calibrated brightness value, the second calibrated brightness value, and the relationship.

8. The method of claim 1, further comprising:
displaying the content using the adjusted brightness value.

9. The method of claim 1, further comprising:
determining that the first brightness value and the second brightness value of the display can be calibrated and adjusted using a pupil size of the user based at least in part on a dilation time associated with a dilation of a pupil of the user.

10. The method of claim 1, further comprising:
displaying the content using the adjusted brightness value; and
measuring a pupil size of the user, after displaying the content using the adjusted brightness value, to confirm whether the adjusted brightness value is correctly calibrated for the user.

11. A device, comprising:
one or more memories; and
one or more processors, coupled to the one or more memories, configured to:
  obtain a brightness setting of a display screen associated with the device for a user based at least in part on:
    displaying first calibration content that includes one or more first calibration frames with a first background that approximately corresponds to white, and modifying a luminance of the display screen of the device while displaying the first calibration content until a pupil size of the user satisfies a first target pupil size, and
    displaying second calibration content that includes one or more second calibration frames with a second background that approximately corresponds to black, and modifying the luminance of the display screen while displaying the second calibration content until the pupil size of the user satisfies a second target pupil size;
  calculate a metric value based at least in part on pixel values of content to be displayed;
  adjust the luminance for the display screen based at least in part on the metric value and in accordance with the brightness setting; and
  display, via the display screen and using the adjusted luminance, the content.

12. The device of claim 11, wherein the brightness setting includes a first pupil size and a first luminance of the display screen optimized for the user for the first calibration content, and a second pupil size and a second luminance of the display screen optimized for the user for the second calibration content.

13. The device of claim 12, wherein the one or more processors, to adjust the luminance, are configured to:
determine a relationship between the metric value, a first pixel value associated with the first calibration content, and a second pixel value associated with the second calibration content; and
determine the luminance for the display screen based at least in part on the first luminance, the second luminance, and the relationship.

14. The device of claim 12, wherein the one or more processors are further configured to:
measure the pupil size of the user after displaying the content using the adjusted luminance;
determine whether the brightness setting is accurate for the user based at least in part on the pupil size of the user after displaying the content, the first pupil size, and the second pupil size; and
re-calibrate the brightness setting based at least in part on determining that the brightness setting is not accurate.

15. The device of claim 11, wherein the one or more processors, to obtain the brightness setting, are configured to:
display the one or more first calibration frames with the first background having a first pixel value and a first animation having a second pixel value; and
display the one or more second calibration frames with the second background having a third pixel value and a second animation having a fourth pixel value.

16. The device of claim 11, wherein the one or more processors, to obtain the brightness setting, are configured to:
receive a user input indicating an adjustment to at least one of:
a first luminance of the display screen calibrated for the first calibration content, or
a second luminance of the display screen calibrated for the second calibration content,
wherein the brightness setting is based at least in part on the user input.

17. The device of claim 11, wherein the one or more processors, to obtain the brightness setting, are configured to:
display the first calibration content using a first luminance of the display screen for a first interval of time;
measure the pupil size of the user after the first interval of time; and
display the first calibration content using a second luminance of the display screen for a second interval of time based at least in part on a difference between the pupil size of the user after the first interval and the first target pupil size not satisfying a threshold.

18. The device of claim 11, wherein the one or more processors, to calculate the metric value, are configured to:
calculate, for a set of pixels of a frame of the content, a set of pixel values based at least in part on red, green, and blue (RGB) triplet values associated with the set of pixels;
calculate, for the frame, a frame pixel value based at least in part on the set of pixel values; and
calculate the metric value based at least in part on averaging frame pixel values, including the frame pixel value, of one or more frames, including the frame, of the content.

19. The device of claim 11, wherein the metric value includes at least one of:
a statistical average of the pixel values of the content,
a first average pixel value of the content,
a local maximum of pixel values of the content in a region of interest,
a local minimum of the pixel values of the content in the region of interest, or
a second average pixel value of the pixel values of the content in the region of interest.

20. The device of claim 11, wherein the one or more processors are further configured to:
determine whether the device is enabled to calibrate the brightness setting using the pupil size of the user based at least in part on comparing an amount of time that a pupil of the user takes to dilate to a dilation time.

21. The device of claim 11, wherein the one or more processors are further configured to:
store the brightness setting as being associated with a user profile associated with the user;
receive a credential associated with the user profile; and
load the brightness setting for a session associated with the user profile based on authenticating the credential.

22. A non-transitory computer-readable medium storing a set of instructions, the set of instructions comprising:
one or more instructions that, when executed by one or more processors of a device, cause the device to:
calibrate a brightness setting of the device for a user based at least in part on:
displaying first calibration content that includes one or more first calibration frames with a first background that approximately corresponds to white while adjusting a first brightness value of a display screen of the device to be a first calibrated brightness value that achieves a first target pupil size of the user,
displaying second calibration content that includes one or more second calibration frames with a second background that approximately corresponds to black while adjusting a second brightness value of the display screen of the device to be a second calibrated brightness value that achieves a second target pupil size of the user, and
displaying a user input option to adjust at least one of the first calibrated brightness value or the second calibrated brightness value;
calculate a metric value based at least in part on pixel values of content to be displayed; and
display, via the display screen and using an adjusted brightness value, the content, wherein the adjusted brightness value is based at least in part on the metric value and is adjusted in accordance with the brightness setting.

23. The non-transitory computer-readable medium of claim 22, wherein the brightness setting includes a first pupil size and the first calibrated brightness value optimized for the user for the first calibration content, and a second pupil size and the second calibrated brightness value for the user for the second calibration content.

24. The non-transitory computer-readable medium of claim 23, wherein the one or more instructions, when executed by the one or more processors of the device, further cause the device to:

determine a relationship between the metric value, a first pixel value associated with the first calibration content, and a second pixel value associated with the second calibration content; and determine the adjusted brightness value based at least in part on the first calibrated brightness value, the second calibrated brightness value, and the relationship.

25. The non-transitory computer-readable medium of claim 22, wherein the first target pupil size is an optimized pupil size for bright light environments, and wherein the second target pupil size is an optimized pupil size for dark environments.

26. The non-transitory computer-readable medium of claim 22, wherein the one or more instructions, that cause the device to display the content, cause the device to:

determine the adjusted brightness value of the display screen based at least in part on the metric value and the brightness setting and without measuring a pupil size of the user after calibrating the brightness setting.

27. An apparatus, comprising:

means for calibrating a brightness setting of the apparatus for a user based at least in part on:

displaying first calibration content that includes one or more first calibration frames with a first background that approximately corresponds to white and modifying a luminance of a display screen of the apparatus while displaying the first calibration content until a pupil size of the user satisfies a first target pupil size, and displaying second calibration content that includes one or more second calibration frames with a second background that approximately corresponds to black, and modifying the luminance of the display screen while displaying the second calibration content until the pupil size of the user reaches a second target pupil size;

means for calculating a metric value based at least in part on pixel values of content to be displayed by the apparatus; and means for adjusting the luminance for the display screen based at least in part on the metric value and in accordance with the brightness setting.

28. The apparatus of claim 27, wherein the brightness setting includes a first pupil size and a first luminance of the display screen optimized for the user for a first brightness value of the first calibration content, and a second pupil size and a second luminance of the display screen optimized for the user for a second brightness value of the second calibration content.

29. The apparatus of claim 28, wherein the means for adjusting the luminance for the display screen comprise:

means for determining a relationship between the metric value, a first pixel value associated with the first calibration content, and a second pixel value associated with the second calibration content; and means for determining the luminance for the display screen based at least in part on the first luminance, the second luminance, and the relationship.

30. The apparatus of claim 28, further comprising:

means for measuring the pupil size of the user after displaying the content using the adjusted luminance;

means for determining whether the brightness setting is accurate for the user based at least in part on the pupil size of the user after displaying the content, the first pupil size, and the second pupil size; and means for re-calibrating the brightness setting based at least in part on determining that the brightness setting is not accurate.

\* \* \* \* \*